United States Patent
Wang et al.

(10) Patent No.: US 10,431,327 B2
(45) Date of Patent: *Oct. 1, 2019

(54) COMPUTER GRAPHICAL USER INTERFACE WITH GENOMIC WORKFLOW

(71) Applicant: Palantir Technologies, Inc., Palo Alto, CA (US)

(72) Inventors: Lekan Wang, Palo Alto, CA (US); Hyunghoon Cho, Stanford, CA (US); Abimanyu Raja, Stanford, CA (US); Elizabeth Caudill, Menlo Park, CA (US)

(73) Assignee: Palantir Technologies Inc., Palo Alto, CA (US)

( * ) Notice: Subject to any disclaimer, the term of this patent is extended or adjusted under 35 U.S.C. 154(b) by 291 days.

This patent is subject to a terminal disclaimer.

(21) Appl. No.: 15/339,666

(22) Filed: Oct. 31, 2016

(65) Prior Publication Data
US 2017/0046481 A1    Feb. 16, 2017

Related U.S. Application Data

(63) Continuation of application No. 13/831,791, filed on Mar. 15, 2013, now Pat. No. 9,501,202.

(51) Int. Cl.
*G06F 19/26* (2011.01)
*G06F 19/28* (2011.01)
(Continued)

(52) U.S. Cl.
CPC ........... *G16B 45/00* (2019.02); *G06F 3/0481* (2013.01); *G06F 3/0482* (2013.01);
(Continued)

(58) Field of Classification Search
CPC .......... G06F 19/22; G06F 19/26; G06F 17/30; G06F 19/28; G06F 3/0482; G06F 3/0484
See application file for complete search history.

(56) References Cited

U.S. PATENT DOCUMENTS 5,893,072 A   4/1999 Zizzamia
6,232,971 B1  5/2001 Haynes
(Continued)

FOREIGN PATENT DOCUMENTS

AU  2014200965    7/2018
DE  102014103476  9/2014
(Continued)

OTHER PUBLICATIONS

Official Communication for European Patent Application No. 15156004.2 dated Aug. 24, 2015.
(Continued)

*Primary Examiner* — Sang H Kim
(74) *Attorney, Agent, or Firm* — Hickman Palermo Becker Bingham LLP

(57) ABSTRACT

Methods and computer apparatuses are disclosed for processing genomic data in at least partially automated workflows of modules. A method comprises: specifying a source from which nucleic acid sequence(s) are to be obtained; selecting module(s) for processing data, including at least one module for processing the one or more nucleic acid sequences; presenting, in a graphical user interface, graphical components representing the source and the module(s) as nodes within a workspace; receiving, via the graphical user interface, inputs arranging the source and the module(s) as a workflow comprising a series of nodes, the series indicating, for each particular module, that output from one of the source or another particular module is to be input into the particular module; generating an output for the workflow based upon the nucleic acid sequence(s) by processing each module in an order indicated by the series.

20 Claims, 15 Drawing Sheets

(51) Int. Cl.

| | | |
|---|---|---|
| *G06F 17/30* | (2006.01) | |
| *G06F 3/0482* | (2013.01) | |
| *G06F 3/0484* | (2013.01) | |
| *G16B 45/00* | (2019.01) | |
| *G06F 16/951* | (2019.01) | |
| *G16B 50/00* | (2019.01) | |
| *G06F 3/0481* | (2013.01) | |
| *G06Q 10/10* | (2012.01) | |

(52) U.S. Cl.
CPC ........ *G06F 3/04847* (2013.01); *G06F 16/951* (2019.01); *G06Q 10/10* (2013.01); *G16B 50/00* (2019.02)

(56) References Cited

U.S. PATENT DOCUMENTS

| | | | |
|---|---|---|---|
| 6,505,196 | B2 | 1/2003 | Drucker et al. |
| 6,523,019 | B1 | 2/2003 | Borthwick |
| 7,383,239 | B2 | 6/2008 | Bonissone |
| 7,418,431 | B1 | 8/2008 | Nies et al. |
| 7,765,489 | B1 | 7/2010 | Shah |
| 7,813,937 | B1 | 10/2010 | Pathria et al. |
| 7,827,045 | B2 | 11/2010 | Madill et al. |
| 7,966,199 | B1 | 6/2011 | Frasher |
| 8,214,232 | B2 | 7/2012 | Tyler et al. |
| 8,301,464 | B1 | 10/2012 | Cave et al. |
| 8,489,623 | B2 | 7/2013 | Jain et al. |
| 8,515,912 | B2 | 8/2013 | Garrod et al. |
| 8,527,461 | B2 | 9/2013 | Ducott, III et al. |
| 8,578,500 | B2 | 11/2013 | Long |
| 8,639,522 | B2 | 1/2014 | Pathria et al. |
| 8,655,687 | B2 | 2/2014 | Zizzamia |
| 8,682,696 | B1 | 3/2014 | Shanmugam |
| 8,799,313 | B2 | 8/2014 | Satlow |
| 9,501,202 | B2 | 11/2016 | Wang et al. |
| 2003/0036927 | A1 | 2/2003 | Bowen |
| 2003/0163352 | A1 | 8/2003 | Surpin et al. |
| 2004/0126840 | A1* | 7/2004 | Cheng .................... G06F 19/28 435/69.1 |
| 2005/0028094 | A1 | 2/2005 | Allyn |
| 2005/0108063 | A1 | 5/2005 | Madill et al. |
| 2005/0125715 | A1 | 6/2005 | Di Franco et al. |
| 2005/0149527 | A1 | 7/2005 | Berlin |
| 2006/0080139 | A1 | 4/2006 | Mainzer |
| 2006/0129746 | A1 | 6/2006 | Porter |
| 2006/0142949 | A1 | 6/2006 | Helt |
| 2006/0149596 | A1 | 7/2006 | Surpin et al. |
| 2006/0178915 | A1 | 8/2006 | Chao |
| 2006/0241974 | A1 | 10/2006 | Chao et al. |
| 2007/0136095 | A1 | 6/2007 | Weinstein |
| 2007/0192143 | A1 | 8/2007 | Krishnan et al. |
| 2007/0299697 | A1 | 12/2007 | Friedlander et al. |
| 2008/0155440 | A1* | 6/2008 | Trevor ................... G06Q 30/02 715/769 |
| 2008/0172257 | A1 | 7/2008 | Bisker et al. |
| 2008/0195417 | A1 | 8/2008 | Surpin et al. |
| 2008/0195421 | A1 | 8/2008 | Ludwig et al. |
| 2008/0249820 | A1 | 10/2008 | Pathria |
| 2008/0281819 | A1 | 11/2008 | Tenenbaum et al. |
| 2009/0043801 | A1 | 2/2009 | LeClair |
| 2009/0070162 | A1* | 3/2009 | Leonelli ................. G06Q 10/06 705/7.27 |
| 2009/0281839 | A1 | 11/2009 | Lynn et al. |
| 2010/0280851 | A1 | 11/2010 | Merkin |
| 2010/0324929 | A1 | 12/2010 | Petrasich et al. |
| 2011/0161409 | A1 | 6/2011 | Nair |
| 2011/0179048 | A1 | 7/2011 | Satlow |
| 2011/0246229 | A1 | 10/2011 | Pacha |
| 2012/0004894 | A1 | 1/2012 | Butler |
| 2012/0084184 | A1 | 4/2012 | Raleigh |
| 2012/0136764 | A1* | 5/2012 | Miller .................. G06Q 40/123 705/31 |
| 2012/0197657 | A1 | 8/2012 | Prodanovic |
| 2012/0197660 | A1 | 8/2012 | Prodanovic |
| 2013/0006655 | A1 | 1/2013 | Van Arkel et al. |
| 2013/0006668 | A1 | 1/2013 | Van Arkel et al. |
| 2013/0276799 | A1 | 10/2013 | Davidson |
| 2013/0338934 | A1* | 12/2013 | Asadi ..................... G16B 30/00 702/20 |
| 2014/0052466 | A1 | 2/2014 | Deville et al. |
| 2014/0058754 | A1 | 2/2014 | Wild |
| 2014/0081652 | A1 | 3/2014 | Klindworth |
| 2014/0136237 | A1 | 5/2014 | Anderson et al. |
| 2014/0149130 | A1 | 5/2014 | Getchius |
| 2014/0214579 | A1 | 7/2014 | Shen et al. |
| 2014/0244284 | A1 | 8/2014 | Smith |
| 2014/0372953 | A1* | 12/2014 | Laurance ............ G06F 3/04817 715/835 |
| 2015/0186821 | A1 | 7/2015 | Wang et al. |
| 2015/0187036 | A1 | 7/2015 | Wang et al. |
| 2015/0235334 | A1 | 8/2015 | Wang et al. |
| 2016/0034578 | A1 | 2/2016 | Wang et al. |

FOREIGN PATENT DOCUMENTS

| | | |
|---|---|---|
| EP | 2980748 | 2/2016 |
| GB | 2514239 | 11/2014 |
| WO | WO 2008/113059 | 9/2008 |
| WO | WO 2010/030913 | 3/2010 |

OTHER PUBLICATIONS

Kitts, Paul, "Chapter 14: Genome Assembly and Annotation Process," The NCBI Handbook, Oct. 2002, pp. 1-21.
Official Communication for European Patent Application No. 15179122.5 dated Sep. 11, 2015.
Official Communication for Netherlands Patent Application No. 2012437 dated Sep. 18, 2015.
Definition "Overlay", downloaded Jan. 22, 2015, 1 page.
Canese et al., "Chapter 2: PubMed: The Bibliographic Database," The NCBI Handbook, Oct. 2002, pp. 1-10.
Definition "Identify", downloaded Jan. 22, 2015, 1 page.
"A Quick Guide to UniProtKB Swiss-Prot & TrEMBL," Sep. 2011, pp. 2.
Alur et al., "Chapter 2: IBM InfoSphere DataStage Stages," IBM InfoSphere DataStage Data Flow and Job Design, Jul. 1, 2008, pp. 35-137.
Official Communication for Great Britain Patent Application No. 1404573.6 dated Sep. 10, 2014.
Delcher et al., "Identifying Bacterial Genes and Endosymbiont DNA with Glimmer," BioInformatics, vol. 23, No. 6, 2007, pp. 673-679.
Sigrist, et al., "PROSITE, a Protein Domain Database for Functional Characterization and Annotation," Nucleic Acids Research, 2010, vol. 38, pp. D161-D166.
Sirotkin et al., "Chapter 13: The Processing of Biological Sequence Data at NCBI," The NCBI Handbook, Oct. 2002, pp. 1-11.
Mizrachi, Ilene, "Chapter 1: Gen Bank: The Nuckeotide Sequence Database," The NCBI Handbook, Oct. 2002, pp. 1-14.
"The FASTA Program Package," fasta-36.3.4, Mar. 25, 2011, pp. 29.
Madden, Tom, "Chapter 16: The BLAST Sequence Analysis Tool," The NCBI Handbook, Oct. 2002, pp. 1-15.
Notice of Acceptance for Australian Patent Application No. 2014200965 dated Feb. 28, 2018.
Current Claims in application No. 2,845,606, dated Dec. 2018, 5 pages.
Canadian Intellectual Patent Office, "Search Report" in application No. 2,845,606, dated Dec. 5, 2018, 8 pages.

* cited by examiner

COMPUTER GRAPHICAL USER INTERFACE WITH GENOMIC WORKFLOW

BENEFIT CLAIM

This application claims the benefit under 35 U.S.C. §120 as a continuation of application Ser. No. 13/831,791, filed Mar. 15, 2013, the entire contents of which is hereby incorporated herein by reference for all purposes as if fully set forth herein. The applicant(s) hereby rescind any disclaimer of claim scope in the parent application(s) or the prosecution history thereof and advise the USPTO that the claims in this application may be broader than any claim in the parent applications.

FIELD OF THE INVENTION

The present invention relates to data processing techniques for genomic data, such as data describing nucleic acid sequences.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

A wide variety of genomic data exists, including, without limitation, data structures such as DNA sequences and protein sequences, annotations to those structures, and publications. Genomic data may be found in a wide variety of sources. For example, sequence data is one type of genomic data. Common sources of sequence data include web-based databases such as GenBank, provided by the United States National Institute of Health, the European Nucleotide Archive ("ENA"), and the Protein Data Bank, operated by the Research Collaboratory for Structural Bioinformatics. These sources allow users to access sequence data in a number of formats, such as flat-text files or FASTA-formatted files. Generally, the sequence data comprises a header with a sequence identifier and other metadata, and a body comprising a sequence. The sequence data may be accessed in a variety of manners, including in pages on a website, in files downloadable via HTTP and/or FTP protocols, or using a REST-based application programming interface.

Another type of genomic data is annotations. Annotations may include, for example, research findings that are related to specific sites of a sequence, such as an observation that a site is a binding site for a certain protein or a variation of a certain disease. The UC Santa Cruz (UCSC) Genome Browser is a popular web-based interface with which to access various sources of annotation data. Each sequence identifier may be associated with one or more annotation records, and each record may be associated with one or more specific sites in a sequence.

There are also a wide variety of tools for processing genomic data. For example, one common category of tools aligns sequences together and compares those sequences. Some such tools are described in "Computer Graphical User Interface Supporting Aligning Genomic Sequences", application Ser. No. 13/835,688, filed Mar. 15, 2013, the contents of which are hereby incorporated by reference for all purposes, as if set forth in their entirety. Another example tool is BLAST, a web-based tool for identifying similarities between an unknown protein and known proteins. A number of example algorithms for processing genomic data are described in "Biological Sequence Analysis: Probabilistic Models of Proteins and Nucleic Acids" by Richard Durbin, Cambridge University Press 1998, the entire contents of which are hereby incorporated by reference for all purposes as if set forth in their entirety herein. These and other tools generally identify genomic data to process based on input, such as input specifying sequences or input based upon which sequences may be mined or derived. The tools then perform one or more various processing algorithms with respect to the genomic data, such as statistical analyses, comparisons, search operations, filtering operations, manipulations, and so forth. The tools then generate a report of any result(s) of the processing.

The analysis of genomic data has become an increasingly important task. Unfortunately, such analyses are often complex, relying on large quantities of disparate data sources and disconnected tools. For example, a researcher may be interested in determining how variations in a certain genomic sequence affect a certain disease. The researcher may begin the analysis by retrieving a sequence from a databank. The researcher may then code the sequence as a protein using a first tool, compute variations of the protein using a second tool, and run a large-scale similarity search across yet a different databank to find species that have similar proteins. The researcher may then access yet other tools and databanks to search for sequences in these species that code for the protein, and finally execute a motif-finding algorithm to identify other proteins that bind to the protein. As a consequence of the complexity of this task, the researcher's work may be disorganized and difficult to reproduce or extend to other sequences.

While this application will often refer to genomic data, many of the techniques described herein are in fact applicable to any type of data. Other uses of the techniques described herein may include, without limitation, data analyses in the field of natural language processing, social sciences, financial data, historical and comparative linguistics, and marketing research.

DETAILED DESCRIPTION

Figure 1:
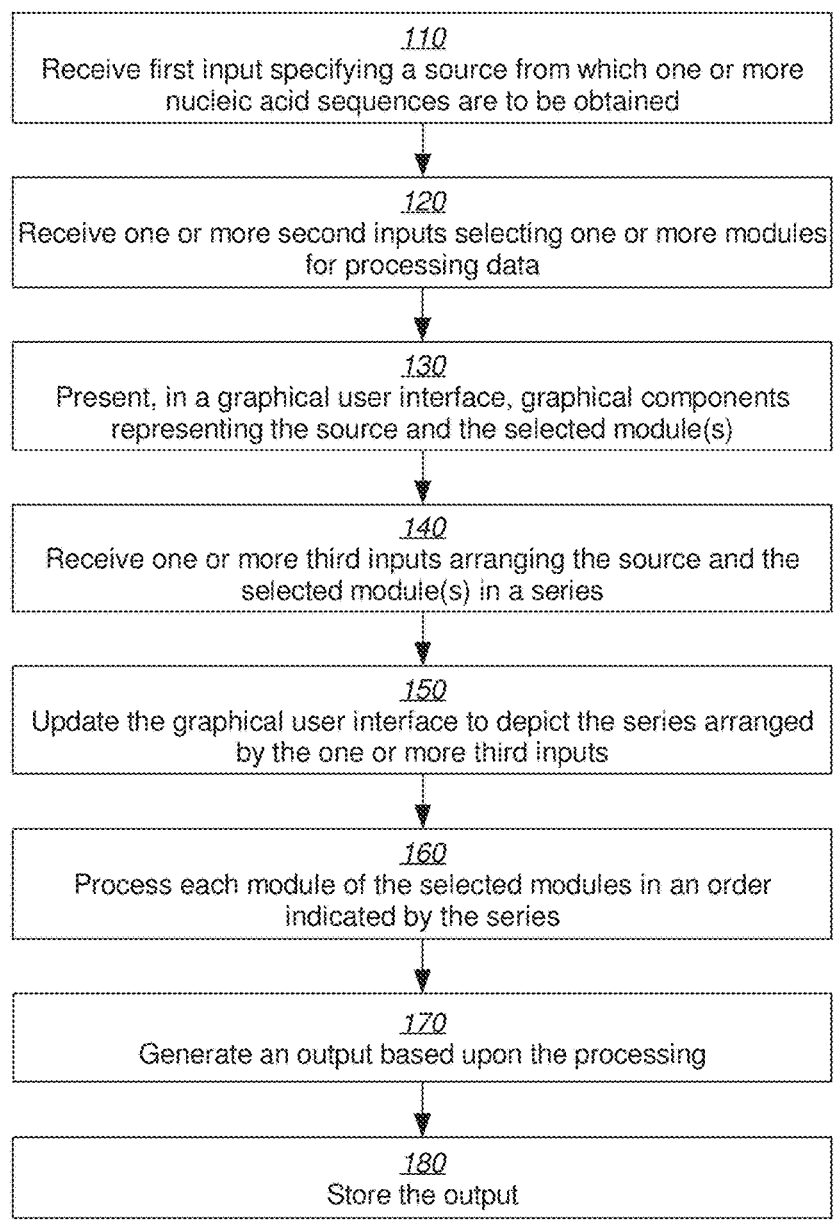
FIG. 1 illustrates an example flow for utilizing a workflow.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

1.0. General Overview

Methods and computer apparatuses are disclosed for processing genomic data in at least partially automated workflows of modules. According to an embodiment, a method comprises: receiving first input specifying a source from which one or more nucleic acid sequences are to be obtained. The method further comprises receiving one or more second inputs selecting one or more modules for processing data, including at least one module for processing the one or more nucleic acid sequences. The method further comprises presenting, in a graphical user interface, graphical components representing the source and the one or more modules as nodes within a workspace. The method further comprises receiving, via the graphical user interface, one or more third inputs arranging the source and the one or more modules as a workflow comprising a series of nodes. The series indicates, for each particular module of the selected modules, that output from one of the source or another particular module is to be input into the particular module. The method further comprises generating an output for the workflow based upon the one or more nucleic acid sequences by processing each module of the one or more modules in an order indicated by the series. The method is performed by one or more computing devices.

In an embodiment, each module of the one or more modules generates output that conforms to an ontology defining data structures that represent genomic data. The data structures include at least sequences, protein objects, alignment objects, annotations, and publications.

In an embodiment, the method further comprises generating a data node from the output. The data node comprises items of genomic data. The data node is linked to a last module in the series. The method further comprises receiving, via the graphical user interface, fourth input that adds or removes an item of genomic data from the data node. The method further comprises receiving, via the graphical user interface, fifth input selecting a particular module to process the data node. The method further comprises adding the particular module to the end of the series. The method further comprises generating second output for the workflow based upon the one or more nucleic acid sequences by processing each module in the series, including the particular module, in the order indicated by the series.

In an embodiment, the one or more modules include a plurality of modules, wherein generating the output for the workflow comprises using output from the source as input to a first module, and using output from the first module as input to a second module. In an embodiment, the at least one module is configured to process the one or more nucleic acid sequences by communicating with at least one of an external web server or an external database server.

In an embodiment, the method further comprises saving workflow data describing the series. The method further comprises causing the workflow data to be shared with multiple users. The method further comprises subsequently reconstructing the series in a second graphical user interface based on the workflow data. The method further comprises receiving fourth input, via the second graphical user interface, modifying the series to include one or more additional modules. The method further comprises generating second output based upon the one or more nucleic acid sequences by processing each module in the series, including the one or more additional modules, in an order indicated by the series.

In an embodiment, the one or more modules include a first module that generates first output based upon the source, and a second module that merges the first output with second output from a third module that is not in the series, wherein the source, first module, second module, and third module are all nodes within a workflow. In an embodiment, the method further comprises presenting controls for selecting the one or more modules, wherein the controls include at least: a first control for selecting a first module that searches for publications in an online database based on genomic data, a second control for selecting a second module that outputs a sequence alignment for multiple sequences, and a third control for selecting a third module that identifies protein families for a nucleic acid sequence.

In an embodiment, receiving the one or more third inputs comprises presenting visual feedback while a first node is selected that indicates that genomic data output from the first node can be linked as input to a second node. In an embodiment, the one or more modules include at least two modules, and processing each module of the one or more modules in an order indicated by the series comprises automatically processing each module, without human intervention between beginning processing of a first module in the series and generating the output by concluding processing of a last module in the series.

In other aspects, the invention encompasses a computer apparatus and a computer-readable medium configured to carry out the foregoing steps.

2.0. Functional Overview

In an embodiment, the processing and study of genomic data is greatly simplified using a construct herein described as a "workflow." Rather than manually performing each step of a research or data processing task, or rather than writing a proprietary script to perform these steps, a researcher may utilize the techniques described herein to generate a re-usable and easily modifiable workflow that chains these disparate steps together in an interconnected construct, and performs some or all of the steps of a task in an automated fashion, with minimal or no user intervention.

2.1. Workflows

As used herein, a workflow is a set of linked nodes that represent sets of data, and actions that are to be performed on those sets of data. In general, the linked nodes form one or more ordered series of nodes. Certain nodes in a series represents an action, while other nodes represent data that has been output from an action represented by a previous node in the series and/or input to an action represented by a next node in the series. For example, the first node of a workflow may represent a mining operation that pulls data from a source, the second node of the workflow may represent the data output by that source, the third node of the workflow may represent an action to be performed on that data, the fourth node may represent a data set that results from that action, and so forth.

A workflow may comprise any arbitrary number of nodes. However, the utility of the workflow model is generally best realized in a series of nodes that comprises two or more action nodes. Furthermore, a workflow may feature branches. Some of these branches may merge. For example, multiple actions may produce a single data set, or multiple data sets may be input into a single action. Other branches split. For example, a data set may be input into two separate actions, or an action may produce multiple similar or dissimilar data sets.

One example implementation of workflows is described in "Document-Based Workflows," U.S. 2010/0070464, published Mar. 18, 2010. "Document-based workflows" describes workflows in which a single node type, referred to as a document, can function as an action node and/or a data node, within the meanings presented herein. Therefore, many of the techniques described therein are applicable to the workflows described herein. The contents of "Document-based workflows" are hereby incorporated by reference for all purposes, as if set forth in their entirety herein.

Data Nodes

Workflow nodes that represent data are referred to herein as data nodes. Data nodes may include data sets imported from a data source, such as a sequence database or publications library, search results, manually inputted data from a user, and/or output data from an action node. The data sets represented by a data node are one or more similarly-typed items. For example, a data set may be an array of items. Items may include any type of data structure. For example, in the context of genomic data example items include, without limitation, sequences, publications, annotations, gene data structures, protein data structures, motif data structures, disease data structures, patient data structures, and so forth. A data node may directly comprise the data set it represents, or a data node may indirectly comprise the data set by referencing location(s) where the data set is found. A data node may further comprise metadata describing the data set, such as a data type to which the items in the data set conform, summary data, research notes, and/or a reference to the original source of the data set, such as database record(s) and/or action node(s).

In an embodiment, a workflow interface may allow a user to interact with any data node in a workflow for observational purposes. Hence, a user may create data nodes in certain positions of a workflow where the user wishes to observe data being processed by the workflow. For example, the workflow interface may represent the data node as a group of named items, with an interactive control corresponding to each item. A user may select the control for an item to access various interfaces for viewing sequences, metadata, analyses, and other information corresponding to the selected item. Data nodes may further facilitate other interactions, as described in other sections.

Action Nodes

Action nodes are nodes that represent actions to be performed on a data set. An action node may represent any type of action supported by a workflow application. Examples of actions that could be represented by action nodes that pertain to genomic data are described in subsequent sections.

In an embodiment, each action node comprises a reference to a specific module that is responsible for performing the node's action, and optionally one or more configuration parameters for that module. A module is a reusable execution unit that performs an action. For example, the module may comprise actual instructions for performing an action based on a specified set of data. Or, the module may comprise instructions for submitting the specified set of data to an external tool, such as an external run-time library or web server, and then retrieving any result. In an embodiment, a workflow application supports an extensible application programming interface, whereby users may define a variety of different types of modules, each performing different actions.

An action node may comprise metadata that links the node to one or more input nodes. The term input node refers to any data node or other action node that generates data upon which a particular action node performs an action. Certain action nodes are not necessarily linked to any input node. These action nodes may nonetheless have an implied or user-configurable data set upon which actions are performed. For example, an action node may perform a query operation on a database, in which case the database constitutes an implied data set upon which the query operation is performed. An action node may also comprise metadata that links the node to one or more output nodes. The term output node refers to any other node, including both data nodes and action nodes, to which data generated by an action performed at a particular node is directed. Some action nodes are not necessarily linked to any output nodes. Such may be the case for action nodes that perform a terminal action such as saving results, or for action nodes that have not yet been executed.

For simplicity, various example workflows are described in terms of their action nodes. However, these workflows may also have intervening data nodes that represent data with which a user may interact.

Typed Data

One obstacle to interoperability between various genomic data tools is the wide variety of formats that the different tools use to structure their results. In an embodiment, workflows simplify this obstacle by converting the outputs of various tools into defined data types. For example, workflows may utilize a set of data types defined by a certain schema or ontology. The schema or ontology may define universal structures to represent common units of genomic data, such as sequences, proteins, annotations, publications, and so forth.

Rather than working with ambiguously formatted flat text files, the inputs and outputs of each workflow node conform to standardized, predictable data types. This is because action modules are required to accept input that conforms to a specified data type, and to generate output that conforms to a specified data type. In an embodiment, particular action modules comprise or are associated with metadata that specifies one or more input or output data types that the action module can handle. A workflow application only allows a user to link a particular action node to other action nodes whose action module handles input or output that conform to these one or more specified input or output data types, or data nodes that comprise data of these one or more specified input or output data types.

To simplify the challenge of utilizing typed data in a workflow, a workflow application may provide various data conversion components. A module may feed output from an external tool to an appropriate conversion component along with information that assists the conversion component in understanding the data, such as the identity of the tool from which the data was retrieved. The conversion component parses the data and generates converted data structures based thereon. Similarly, the workflow application may provide conversion components that convert the converted data into common input formats expected by various tools. Yet other modules may perform such conversions using their own customized code.

2.2. Workflow Process Flow

FIG. 1 illustrates an example flow 100 for utilizing a workflow, according to an embodiment. Flow 100 is but an example flow for utilizing a workflow. Other flows may comprise fewer or additional elements in potentially different arrangements.

Block 110 comprises receiving first input specifying a source from which one or more nucleic acid sequences are to be obtained. The first input defines, in essence, a data node of a workflow. A data node represents a data set, which in this case is the one or more nucleic acids obtained from the source. Example sources include, without limitation, one or more files in a local file system, a web page, a web-based search, one or more database records, an existing workflow, clipboard contents, a library of previously saved sequences, or an action node. Input specifying a source may be received via any suitable user interface technique. An example interface for specifying sources is described in other sections. Input specifying a source may instead be received via textual input, such as in an XML file for a previously saved workflow or via command-line input.

The data node defined by the first input is not necessarily the only data node in the workflow or even the only data node defined in block 110. For example, block 110 may further comprise receiving other input(s) specifying source(s) for other nucleic acid sequences or other types of genomic data.

Block 120 comprises receiving one or more second inputs selecting one or more modules for processing data. The one or more second inputs may select, for example, one or more action modules such as described herein. Hence, each second input defines an action node for the workflow. The one or more second inputs may further specify one or more configuration parameters for the one or more modules, if needed. The action nodes defined by the one or more second inputs are not necessarily all of the action nodes within a workflow, and block 120 may further comprise receiving other input(s) defining other action node(s).

Like the first input, each second input may be received via any suitable user interface technique, including those described in other sections, or via textual input. In an embodiment, the modules are selected from a set of pre-defined modules. In an embodiment, the pre-defined modules may include both modules provided by a provider of a workflow application, and user-created modules. In an embodiment, a second input selects a module that is not pre-defined, but rather created by the second input. For example, a user may provide code or other instructions for a non-reusable module while defining the workflow.

Block 130 comprises presenting, in a graphical user interface, graphical components representing the source and the selected modules. The presentation may comprise, for example, separate icons or other graphical representations for the source and for each module. The complexity of the graphical components may vary from embodiment to embodiment. For example, some embodiments may represent a source using a simple icon, while other embodiments may represent a source by listing, within the graphical component corresponding to the source, identifiers for some or all of the data items that belong to the source. Examples of suitable graphical components are described herein.

In an embodiment, a workflow application may perform block 130. The workflow application identifies the source and module(s) specified by the first and second inputs. The workflow application then generates a visual presentation of the source and module(s) within an application workspace. The application workspace represents a workflow, to which the source and the selected module(s) are deemed to belong.

In an embodiment, blocks 110-130 occur concurrently. For example, a user may provide the first input, and the workflow application may immediately respond by displaying a graphical component for the source. The user may subsequently provide each second input, and the workflow application creates a new graphical component in response to each second input.

Block 140 comprises receiving one or more third inputs arranging the source and the one or more modules in a series. For example, the one or more third inputs may comprise a fourth input that establishes the source as a first node in a series, and additional inputs that link the one or more modules in a succession following the source. Like the first input, each third input may be received via any suitable user interface technique, including those described in other sections, or via textual input. In an embodiment, the one or more third inputs are received via the graphical user interface. For example, a third input may comprise dragging a cursor from an output connector associated with a graphical representation of the source to an input connector associated with a graphical representation of a module.

The series indicates that for each particular module of the selected modules, output from one of the source or another particular module is to be input into the particular module. The series may in fact comprise more nodes than just the source and the one or more modules. For example, the source and module(s) may have been arranged to follow an existing series of nodes, and/or other nodes may be arranged to follow the source and the module(s). Moreover, the workflow may in fact comprise multiple series of nodes. For example, a workflow may comprise two series that are entirely detached from each other, or the workflow may comprise a series that branches into or off of a node in another series.

In an embodiment, the one or more third inputs are received via an interface that enforces constraints upon the types of nodes that can be linked. For example, if any input attempts to arrange a module after a source or another module that outputs a data type not supported by the module, the interface will refuse to arrange the module in the manner indicated by the input.

Block 150 comprises updating the graphical user interface to depict the series arranged by the one or more third inputs. For example, the source and module(s) may be re-ordered within the graphical user interface in accordance to the series. Or, the source and module(s) may be connected to each other by lines or other suitable connectors, in an order indicated by the series. In an embodiment, in response to each third input, the graphical user interface updates to depict a new arrangement, rather than waiting for receipt of all of the one or more third inputs.

In an embodiment, blocks 140 and 150 may be performed concurrently with blocks 110-130. For example, the user may add a source and a first module to a workspace, and then link the source to the first module. The user may then add a second module to the workspace, and then link the second module to the original module. The graphical user interface may continually update as the user provides these inputs.

Block 160 comprises processing each module of the selected modules in an order indicated by the series. The processing of modules within a workflow is described in subsequent sections.

Block 170 comprises generating an output based upon this processing. Since the one or more nucleic acid sequences were used as input to at least one module, the output is based at least upon the one or more nucleic acid sequences. Of course, the output may be further based on other data inputs, if so defined, in the workflow. The output is generated by the processing of the last, or second to last, module in the series. Thus, block 160 in essence comprises block 170.

Block 180 comprises optionally storing the output. For example, the output may be saved in a local database or file system. Or, the output may be uploaded to a web-based database. Or, the output may be sent to another user. Block 180 may or may not be performed as part of processing the last module in a series. For example, the last node in a workflow may be an action node that performs the storage operation. Or, the last node in the workflow may be a data node with the output from block 170. In the latter case, block 180 may be performed outside of the processing of the workflow. For example, the user may manually import the data set represented by the last node of the workflow to a database. Or the user may copy and paste the data set into a report, that is then stored to a file.

2.3. Processing a Workflow

In an embodiment, processing a workflow comprises processing a series of nodes. A first action node in the series of nodes corresponds to a first module. Processing the workflow comprises executing the first module based on data input from a data node that represents a source. An output is generated based on the execution of the first module. In an embodiment, the processing further comprises executing a second module represented by a second action node in the series. Based on the output from the first module, a second output is generated based on the execution of the second module. In an embodiment, the processing further comprises iteratively executing each module represented by each subsequent action node in the series, using output from an immediately previous action node as input, until all action nodes in the series have been processed.

In an embodiment, processing a workflow comprises "processing" a data node. The processing of a data node comprises populating the data node with a data set output from a previous action node. The processing of a data node may or may not further comprise receiving interactive user manipulations of the data set, as described below. The data set is passed as input to any subsequent action node.

In an embodiment, processing a workflow comprises processing multiple series of nodes. Any given series or node may be dependent upon output from any other given series or node in the workflow. However, once a node or series upon which another node or series depends has been processed, the other node or series may be executed without regard to the timing of any other node or series. For example, multiple independent series may be executed in parallel with respect to each other, or at any other time relative to each other.

In an embodiment, executing ("processing") a module comprises executing instructions defined for the module. The instructions are optionally executed based upon one or more configuration parameters defined in a second input. In an embodiment, the instructions send a request to an external component, such as a web-based server or external application. The request comprises or references the data input into the module during the processing, which may or may not have been reformatted in accordance to the module's instructions. In response, the module receives data from the external component. The module may optionally reformat or otherwise process the returned data before returning it as output.

Automated Workflows

In an embodiment, some or all workflows are processed automatically, in a non-interactive fashion. Once such a workflow has been defined, processing of the workflow requires no additional user input between the time that the first node is processed and the time that a last module is processed.

Interactive Workflows

While some workflows described herein are designed to produce output without human intervention, other workflows are designed to assist a user in identification processes and determinations, rather than simply produce an output. For such workflows, at various stages of designing and using the workflow, the user may provide various inputs to interact with and/or manipulate the flow of data. A user may, for example, execute a portion of the workflow. Based on output from execution of that portion, the user may decide to execute other portions of the workflow, and/or redefine the workflow to include additional nodes or series of nodes.

In an embodiment, a user may manipulate the data within any data node. Hence, a data node may represent a position in the workflow at which a user may wish to make an informed decision with respect to how the workflow is to proceed. By contrast, for data processing with which the user does not intend to intervene, the workflow does not require a data node. Thus, multiple action nodes may follow each other without intervening data nodes, thereby indicating that the processing of data at those positions is entirely automated. However, since data nodes may also serve observational purposes, the existence of a data node does not necessitate that the user must manipulate data within the data node.

For example, a user may edit a data node by adding or removing items, thereby allowing the user to interactively filter the data set for any subsequent workflow actions for which the data node provides input. The user may "execute" a first portion of a workflow to generate the data node. The user may then edit the data node before proceeding with, or even creating, the second portion of the workflow. Similarly, the user may create new data nodes by moving or copying items from another data node. These new data nodes may then be linked to action nodes within the workflow.

2.4. Re-Using Workflows

In an embodiment, a user may save a workflow for subsequent re-use. For example, a workflow data structure, such as an XML file or other data object, may describe a workflow. A user may save the workflow data structure to a file system or database. The user may subsequently access the workflow data structure in order to execute the workflow again. For instance, the user may load the workflow data structure in a workflow application. The workflow application may present graphical representations of the workflow described by the workflow data structure. The user may then execute the workflow as it was constituted at the time the workflow was saved, or the user may modify the workflow to process potentially different data sources in different manners.

In an embodiment, certain saved workflows may be utilized as templates, from which the user may rapidly create new workflows. In an embodiment, a workflow may be shared with other users. For example, a user may email a workflow, or a link to a workflow, to another user. If the other user has access to the same data sources and same modules—for instance, by means of a centralized resource server—the other user may run and/or tweak the workflow. If the other user does not have access to the same data sources and same modules, various techniques for finding substitute sources and modules may apply. Or, to prevent resource dependency problems, a shared workflow may embed modules and data sources to which another user is not likely to have access.

In an embodiment, a user may configure a saved, non-interactive workflow to run in response to triggers or on a periodic basis. For example, a data source may change periodically or in response to certain events. A user may create and save an automated workflow to, for instance, generate updated report data whenever the data source is changed or reimport data into a database based on the changes. In an embodiment, a process may monitor the output of a automated workflow and provide an update notification to a user whenever the output changes. For example, a user may configure a workflow to run every morning. The workflow may typically pull the same results. The user may request to receive an automated email whenever the workflow output changes. The user may then investigate the new data.

3.0. Structural Overview

Figure 2:
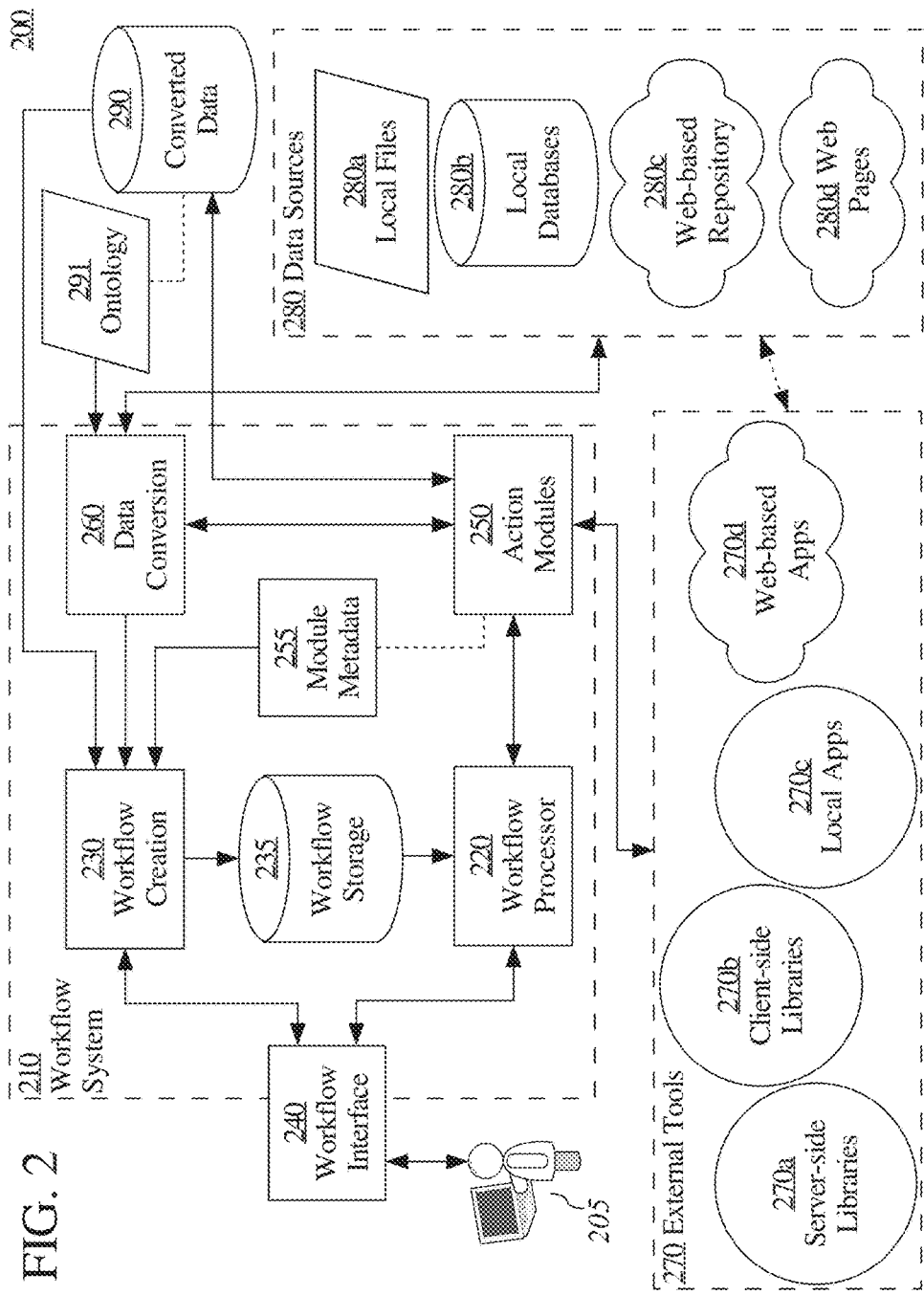
FIG. 2 is a block diagram of an example system in which the techniques described herein may be practiced.

FIG. 2 is a block diagram of an example system 200 in which the techniques described herein may be practiced, according to an embodiment. For example, the various components of system 200 may implement flow 100 as described above.

System 200 comprises a workflow system 210. Workflow system 210 comprises one or more computing devices that implement a series of components 220-260 that provide various functionalities with respect to workflows. For example, workflow system 210 may comprise a client computing device and server computing device. As another example, workflow system 210 may comprise a single computing device. Components 220-260 may be any combination of hardware at the one or more computing devices and software executed by that hardware. In an embodiment, components 220-260 are collectively referred to herein as a "workflow application."

Workflow creation component 230 provides workflow interface component 240 to a user 205. Workflow creation component 230 creates workflows in response to various user input to workflow interface component 240. The various user inputs may, for example, instruct workflow creation component 230 to add data nodes and action nodes to a workflow, manipulate those nodes, and create links between certain nodes. Workflow creation component 230 updates the workflow interface component 240 to depict representations of the nodes and/or links in a workflow as the user input is received.

Workflow creation component 230 creates action nodes that represent action modules 250 for processing workflow data. Action modules 250 are execution units that input and/or output data, as described in other sections. Workflow creation component 230 learns of the availability of these action modules 250, as well as configuration options for and constraints upon the modules 250, by accessing module metadata 255. For example, when a workflow application is first invoked, the workflow application may scan a folder or other metadata 255 for modules 250, and then make any found modules 250 available for use in the action nodes of a workflow. Workflow creation component 230 then generates interface controls in workflow interface component 240 that allow user 205 to create a new action node and associate that action node with one of the modules 250.

Workflow creation component 230 may create a data node based on input from user 205 specifying a data set. Workflow creation component 230 may further create data nodes based on output from processing an action node, such as from an immediately preceding action node in the current flow, or from an action node at the end of a different workflow.

Workflow creation component 230 further creates data nodes based on data selected by a user from one or both of a converted data repository 290, and data sources 280. Workflow creation component 230 retrieves data sets from converted data repository 290 and/or data sources 280. As the data sets are retrieved, data sources 280 are converted by data conversion component 260, thereby yielding uniform, typed data structures. Data sets from converted data repository 290, on the other hand, are already organized as uniform, typed data structures. Workflow creation component 230 presents these data sets to user 205 in workflow interface component 240, and in response receives input that selects specific data items from the data sets that should belong in the data nodes.

Once a workflow has been created, workflow creation component 230 stores a workflow data structure representing the workflow in workflow storage 235. Workflow storage 235 may be, for example, a temporary location in memory, directory in a local file system, or database.

Workflow interface component 240 further includes controls by which user 205 may instruct workflow processing component 220 to process at least a portion of a currently loaded workflow or a workflow in workflow storage 235. For example, workflow interface component 240 may present a "run workflow" and/or "run node" button that causes the workflow processing component 220 to process at least a portion of the workflow currently displayed in workflow interface component 240. Workflow processing component 220 may also or instead run workflows specified by other input, such as command line input or input from a task scheduler.

Workflow processing component 220 executes workflows described by workflow data structures in workflow storage 235, using workflow processing techniques such as described in other sections. In the course of processing a workflow, workflow processing component 220 invokes action modules 250 referenced by action nodes within the workflow. Workflow processing component 220 may pass a typed data set output by a previous node, if one exists, to an invoked action module 250. Most action modules 250 will process one or more instructions with respect to the input data set, and then return an output comprised of typed data to workflow processor 220. In an embodiment, workflow processing component 220 may create and/or update data nodes in the currently processed workflow to include the data sets output by action modules 250. In an embodiment, when workflow processing component 220 is running in an interactive mode, workflow processing component 220 may further update the workflow interface component 240 to display representations of added or updated data nodes. In an embodiment, workflow processing component 220 may be configured to store, print, or display the final output from a workflow to a variety of locations other than workflow interface component 240.

In an embodiment, one or more action modules 250 comprise self-contained instructions for processing a data set. For example, code for relatively common and/or simple operations, such as merging or filtering a data set, may be included directly within a module 250. In an embodiment, an action module 250 processes a data set using only self-contained instructions, without calling any external tools 270. In an embodiment, a module 250 interacts with one or more external tools 270 for processing a data set. The one or more external tools 270 may implement various algorithms for processing genomic data. Action modules 250 send some or all of the input data set, or processed data based thereon, to external tools 270 for processing. Action modules 250 then receive an output in return. Action modules 250 may optionally process an output before returning the output as typed data to workflow processing component 220. In an embodiment, users may supply their own action modules 250 via an API, which the workflows system 210 may also use.

The external tools 270 may include, for example, local runtime libraries 270a, such as redistributable libraries of Java or Python code, that can be invoked directly through procedure calls in an action module 250. The external tools 270 may also include client-side libraries that run within the workflow interface component 240 at the user's computing device. For example, a module 250 may be implemented using client-side JavaScript tools. Such tools may or may not prompt a user for input that will affect the outcome of the module 250. The external tools 270 may also include local application servers 270c and web-based application servers 270d with which an action module 250 may communicate over one or more networks via any suitable protocol, including HTTP, FTP, REST-based protocols, JSON, and so forth. In an embodiment, all action modules 250 are coded objects that extend a common class. The common class implements logic for communicating with each of these four types of external tools 270. In an embodiment, external tools 270 may include other tools not depicted. In an embodiment, some external tools 270 may furthermore communicate with other external tools 270 to produce an output. In an embodiment, some external tools 270 may generate outputs based on requesting data from data sources 280.

Data sources 280 may include any source of data accessible to system 201, including local files 280a, in any of a variety of formats, and queryable local databases 280b. Data sources 280 may further include web-based repositories 280c that are accessible by various web-based interfaces, including SOAP or REST-based interfaces. In an embodiment, to speed up operation of system 210, web-based repositories 280c are cached locally as local files 280a and/or local databases 280b. For example, workflow system 210 may periodically download database dumps from web-based repository 280c. Data sources 280 may further include web pages 280d. For example, action modules 250 and/or data conversion component 260 may feature "screen-scraping" elements for extracting publications or other data from the web pages 280d of certain web sites.

In an embodiment, data output from external tools 270 and data sources 280 must be converted to converted data 290 prior to being processed by workflow system 210. Workflow system 210 may provide a data conversion component 260 to reformat data from external tools 270 and data sources 280 into typed data structures defined by an ontology 291. The ontology 291 may be for any type of data. In an embodiment, an ontology 291 for genomic data comprises the following core data types: sequences, DNA sequences, mRNA sequences, RNA sequences, protein sequences, protein objects, paper objects, alignment objects, and gene objects.

Converted data 290 is then stored at least temporarily, for processing of the workflow, and/or permanently, for subsequent access by users 205 in other workflows and projects. In an embodiment, data conversion component 260 may further convert data back into a form expected by external tools 270 and data sources 280, for use as input to external tools 270, or for storage in data sources 280. In an embodiment, action modules 250 may also or instead be responsible for directly converting some of the data sets sent to or received from a corresponding tool 270. In an embodiment, some action modules 250 may rely directly upon converted data 290, stored permanently in a database, as opposed to data from data sources 280.

System 200 is but one example of a system in which the techniques described herein may be practiced. Other systems may comprise additional or fewer elements, in potentially varying arrangements. For example, one system omits any number of external tool 270 types or data source 280 types. Another system omits converted data 290 and data conversion component 260. Yet another system omits a graphical workflow interface component 240. Many other variations are also possible.

4.0. Example Interfaces and Workflows

Figure 3:
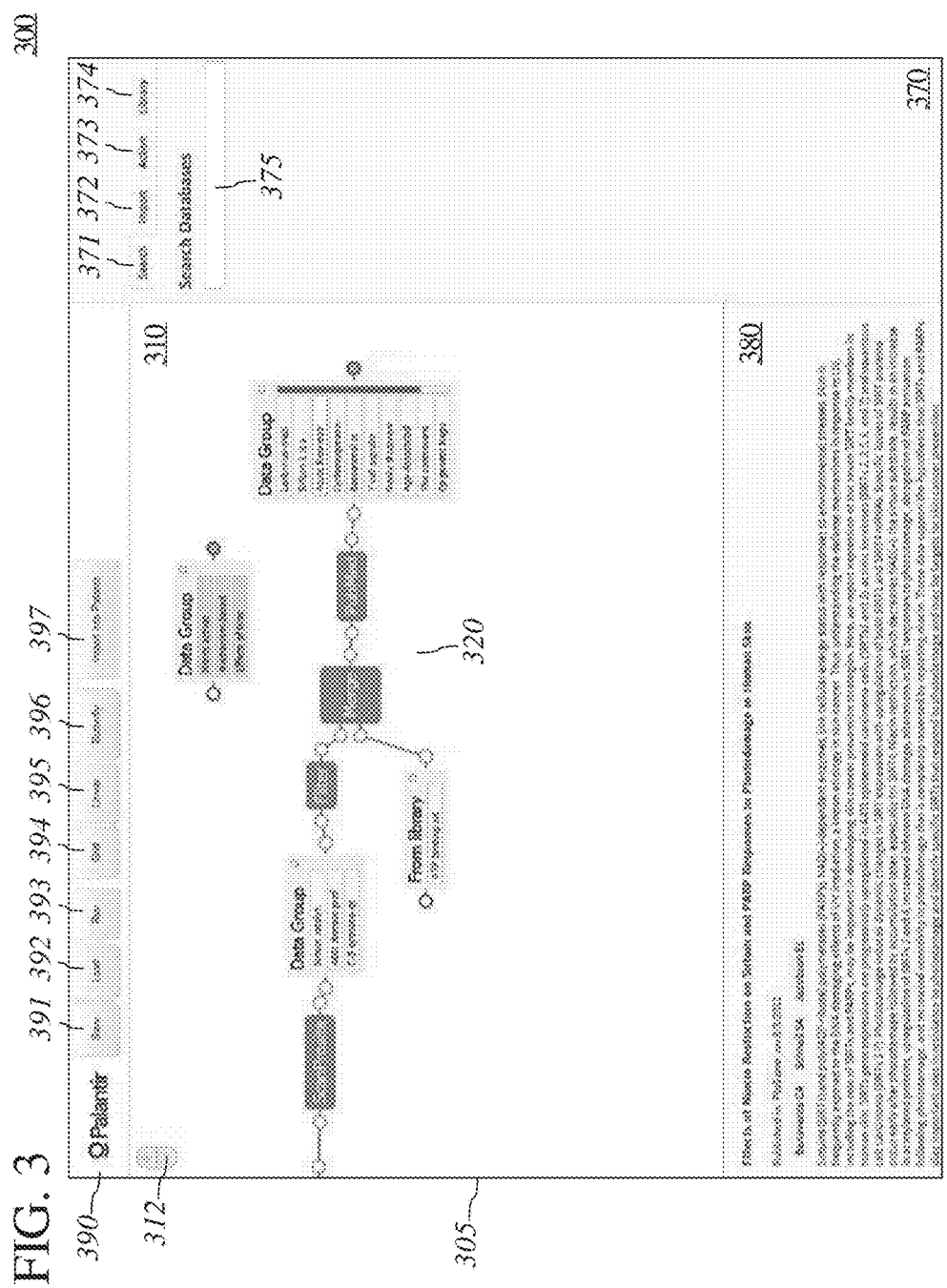
FIG. 3 is a screenshot that illustrates an example interface for practicing techniques described herein.

FIG. 3 is a screenshot 300 that illustrates an example interface 305 for practicing techniques described herein, according to an embodiment. For example, interface 305 may facilitate the receipt of input from a user to define a workflow and/or interact with the processing of a workflow. Interface 305 is an example of a workflow interface component 240.

Interface 305 may comprise various graphical representations of items such as nodes, data items, modules, files, and so forth. To simplify the disclosure, this application sometimes describes graphical interface features in terms of represented items themselves as opposed to the graphical representations of those items. The skilled person will understand that, as is common when describing graphical interfaces, literal descriptions of a graphical interface comprising non-graphical interface components should be interpreted as descriptions of the graphical interface comprising graphical representations of those components. For example, the description may describe a step of "selecting a node from a workspace" when in fact the skilled person will understand that what is being selected is a representation of a node in the workspace.

Interface 305 comprises a workspace area 310 in which is depicted a workflow 320. The various components of workflow 320 are described with respect to subsequent figures. Workspace 310 further comprises zoom controls 312 for enlarging or shrinking the visible area of workspace 310. In an embodiment, the viewable area of workspace 310 is movable through various combinations of cursor inputs and/or selections of scrolling controls.

Interface 305 further comprises a header area 390. Header area 390 includes controls 391-397 for general workflow operations. Save control 391 facilitates input for saving workflow 320. Load control 392 facilitates input for loading a previously stored workflow into workspace 310. Run control 393 facilitates input for processing the entire workflow 320. Or, if a particular one or more nodes of a workflow 320 are currently selected, run control 393 facilitates input for processing a portion of the workflow 320 corresponding to the particular one or more nodes. Controls 394-396 facilitate input for generating different types of presentations based on output from workflow 320. Control 397 facilitates input for importing selected output from workflow 320, including data sets stored in intermediate data nodes, into a data repository.

Interface 305 further comprises a sidebar area 370, which is generally reserved for controls that facilitate the creation of new nodes in workflow 320. Sidebar area 370 comprises four panes 371-374. The currently depicted pane, search pane 371, depicts a database search control 375. Database search control 375 allows a user to perform a term-based search on various databases of genomic data. The user may drag search results, in part or as a whole, to workspace 320 to create new data node(s). Sidebar 370 further includes an import pane 372, an action pane 373, and a library pane 374.

Interface 305 further comprises a summary view area 380. Summary view area 380 generally presents a context-sensitive detail view of information about a currently selected object in workspace 310. For example, as depicted, summary view area 380 presents a "publication view" of a particular publication item that is selected in a data node of workflow 320. Depending on the data type and/or node type of the currently selected item in workspace 320, summary view area 380 may present differently organized views of different fields of information. Some views may contain a single field of information, while other views may contain many fields of information. In an embodiment, the information presented in summary view area 380 is user-definable. Summary view area 380 may be scrollable, depending on which view is presented.

Figure 4:
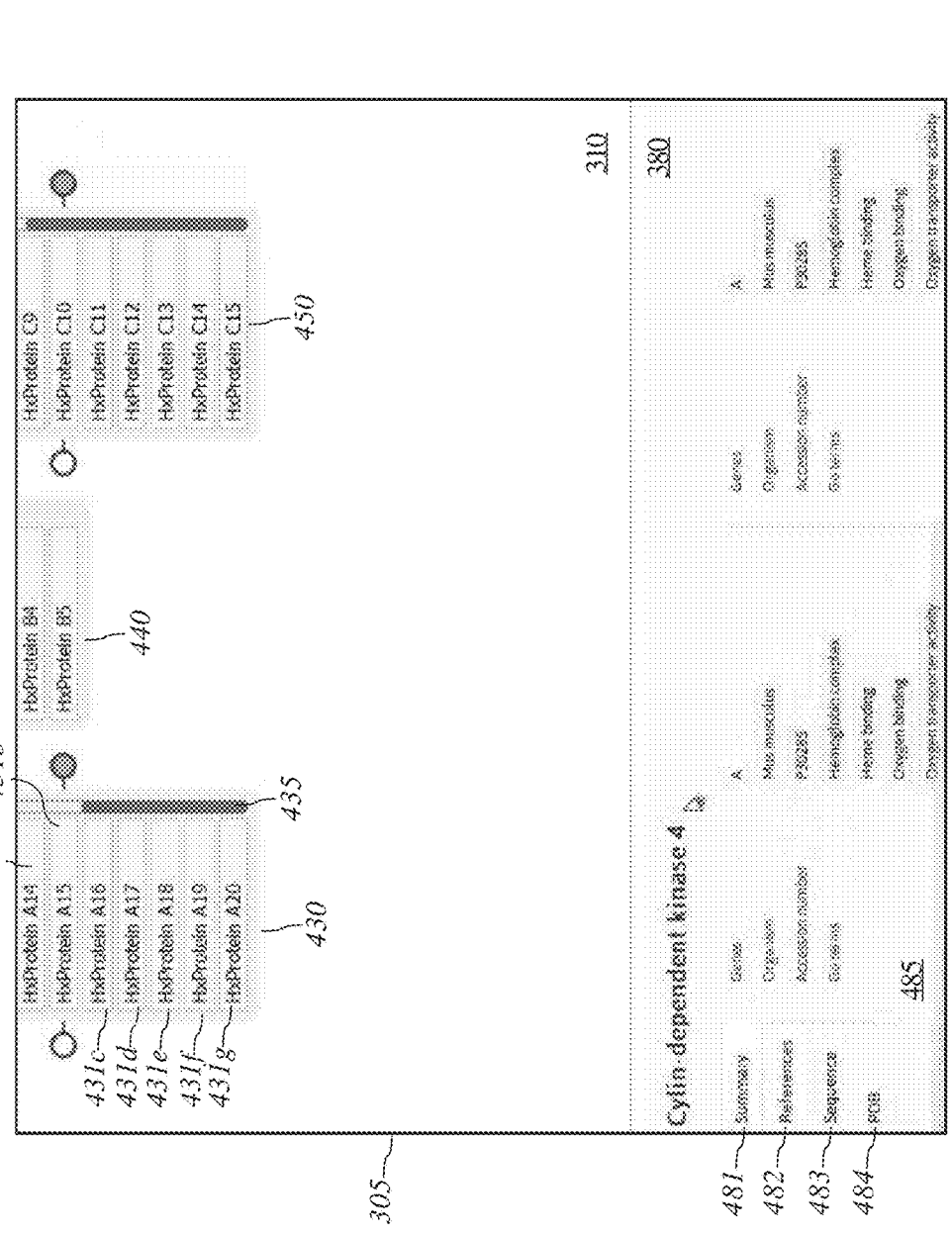
FIG. 4 is a screenshot that illustrates the representation of data nodes in the example interface.

FIG. 4 is a screenshot 400 that illustrates the representation of data nodes in the example interface 305, according to an embodiment. Screenshot 400 shows a portion of workspace 310, including graphical representations of three different data nodes 430-450, and summary view area 380. Each data node 430-450 comprises a set of data items, which are depicted in the respective graphical representations. For example, data node 430 includes at least data items 431a-g, each of which is a different protein object. A user may bring additional data items into view using scroll control 435.

The user may select a particular data item, such as item 431a by clicking on it, or using any other suitable selection technique. In response, summary view area 380 may be updated with a view 485 of information that is associated with the selected item 431a. The information in view 485 may change in response to a user clicking on panes 481-484. Each of panes 481-484 brings into view 485 a different set of information about protein 431a, including summary information (per pane 481), references (per pane 482), sequence data (per pane 483), and PDB data (per pane 484).

A user may also select an entire data node 430-450 by clicking on it, or using any other suitable selection technique. Clicking on a data node may cause summary view area 380 to show a different view of different information than the information depicted in FIG. 4. For example, the view for node 430 may comprise summary information for an entire data set, such as a statistical analysis or histogram showing how similar protein items 431 are to each other.

By contrast, when an action node is selected, the summary view area 380 may comprise metadata describing the module corresponding to the action node, information about the last execution of the module, and/or fields for entering values for configurable parameters of the module.

Figure 5:
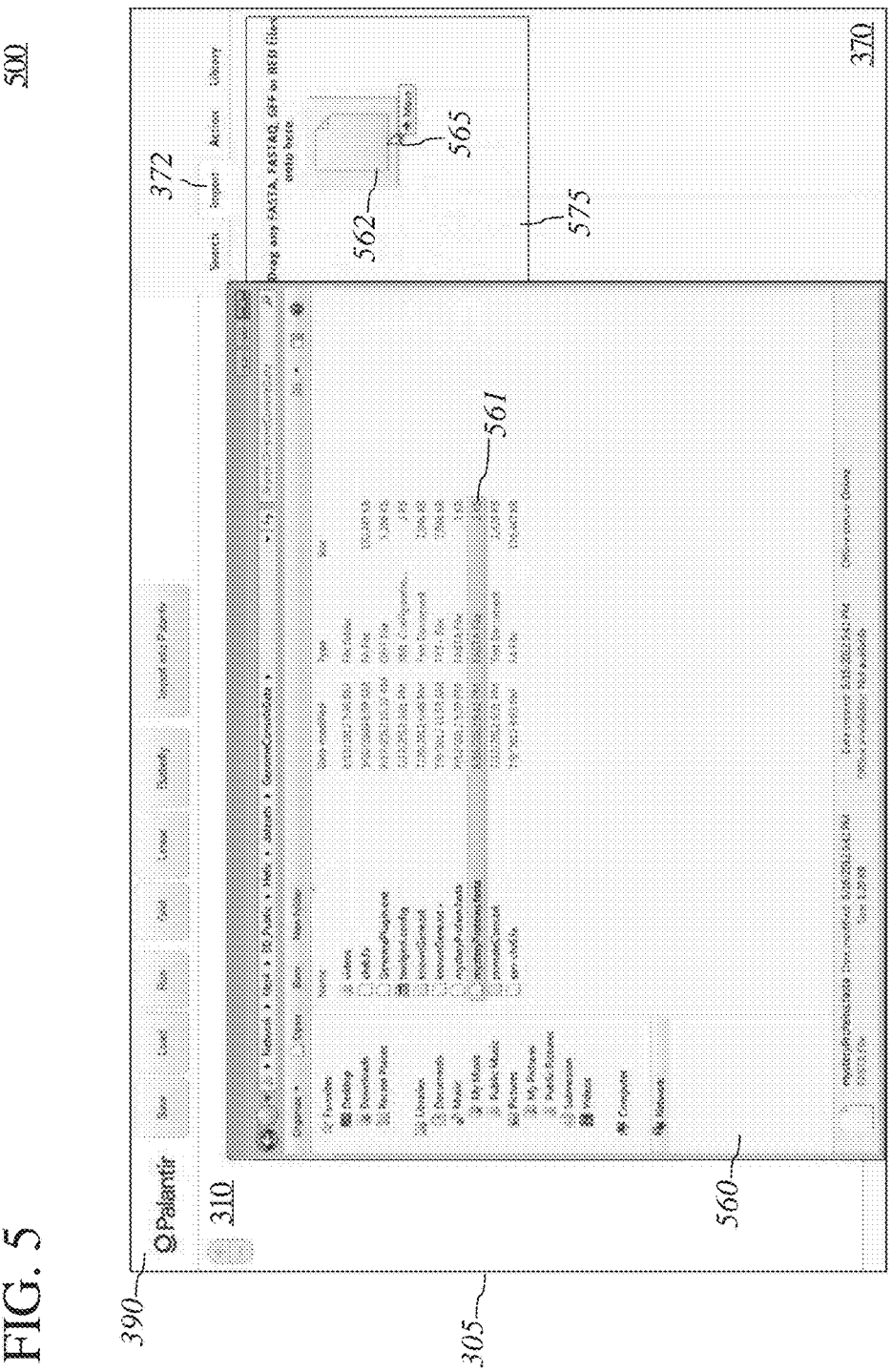
FIG. 5 is a screenshot that illustrates the controls for importing data in the example interface.

FIG. 5 is a screenshot 500 that illustrates controls for importing data in the example interface 305, according to an embodiment. Screenshot 500 shows workspace 310, sidebar 370, and header 390. The import pane 372 has been selected in sidebar 370. Consequently, sidebar 370 displays an import control 575 for receiving input selecting a file. Screenshot 500 further shows a file system explorer window 560 from which a user may select a representation of a file 561. The user may then use cursor 565 to "grab" and "drag" the representation of file 561 over the import control 575. A feedback graphic 562 may be displayed to indicate to the user that the user is in fact dragging file 561 using cursor 565. Once cursor 565 is over import control 575, the user may then "drop" the representation of file 561 in interface area 575 to instruct the user interface 305 to attempt to recognize the file format of file 561, automatically convert the file 561 to one or more data items that may be used in a workflow, and import those data items into the interface 305.

Figure 6:
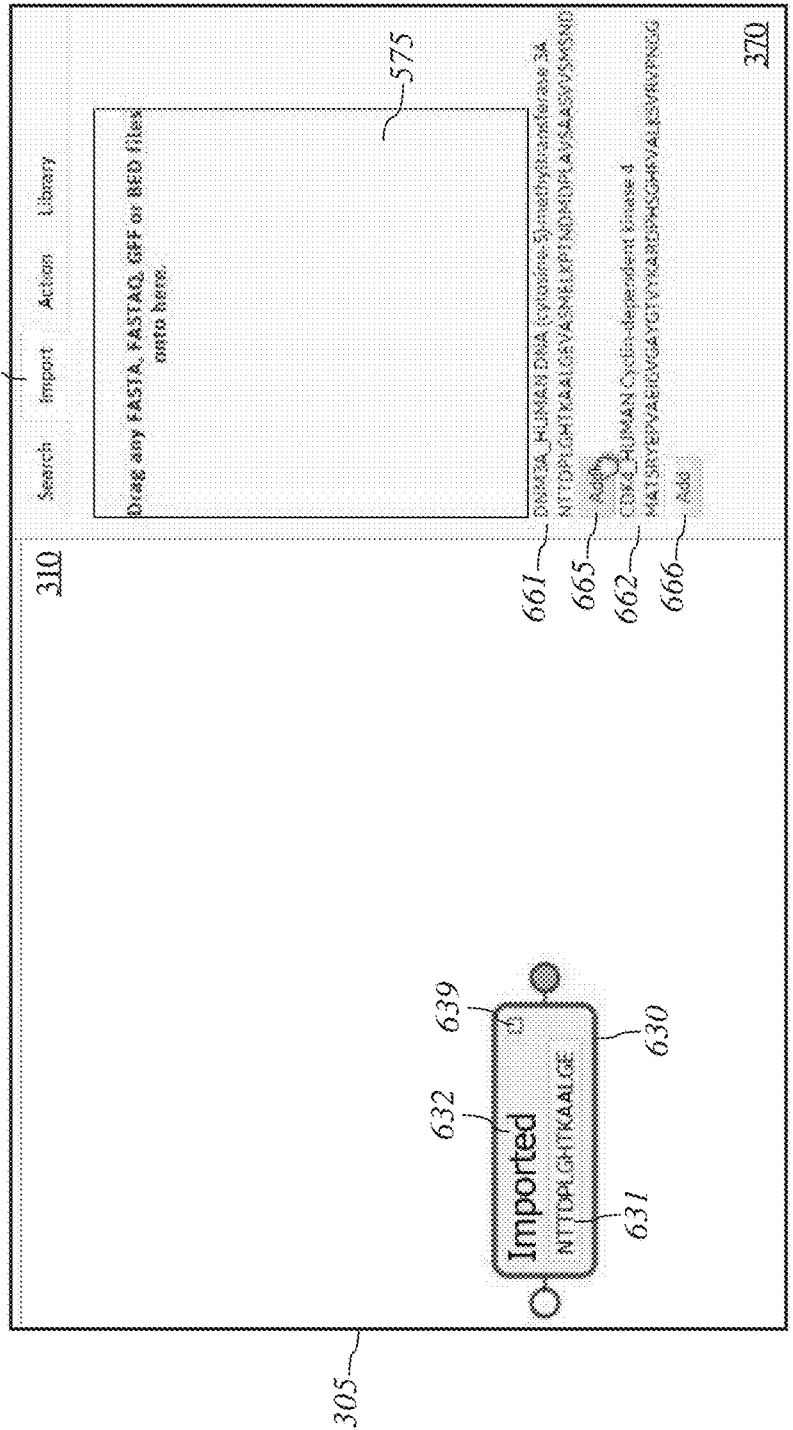
FIG. 6 is a screenshot that illustrates adding a data node to the workspace of the example interface.

FIG. 6 is a screenshot 600 that illustrates adding a data node 630 to the workspace 310 of the example interface 305, according to an embodiment. Screenshot 600 shows portions of workspace 310 and sidebar 370. Sidebar 370 still depicts the import pane 372 with import control 575. Additionally, sidebar 370 includes representations of data items 661 and 662. Data items 661 and 662 are sequences that have been imported from file 561. Adjacent to the representations of data items 661 and 662 are controls 665 and 666 for adding data items 661 and 662, respectively, to a data node that is currently selected within workspace 310. If there is no currently selected data node in workspace 310, a new data node is created when one of controls 665 or 666 is selected.

As depicted in FIG. 6, workspace 310 comprises a representation of the data node 630, which has been created in response to a user clicking on control 665. Thus, as illustrated in the content representation area 631 of node 630, node 630 comprises the imported data item 661. The representation of node 630 further comprises a remove control 639 that causes the removal of node 630 from workspace 310, and a node title 632, which by default refers to the technique by which node 630 came into existence (i.e. the fact that it was "Imported").

Figure 7:
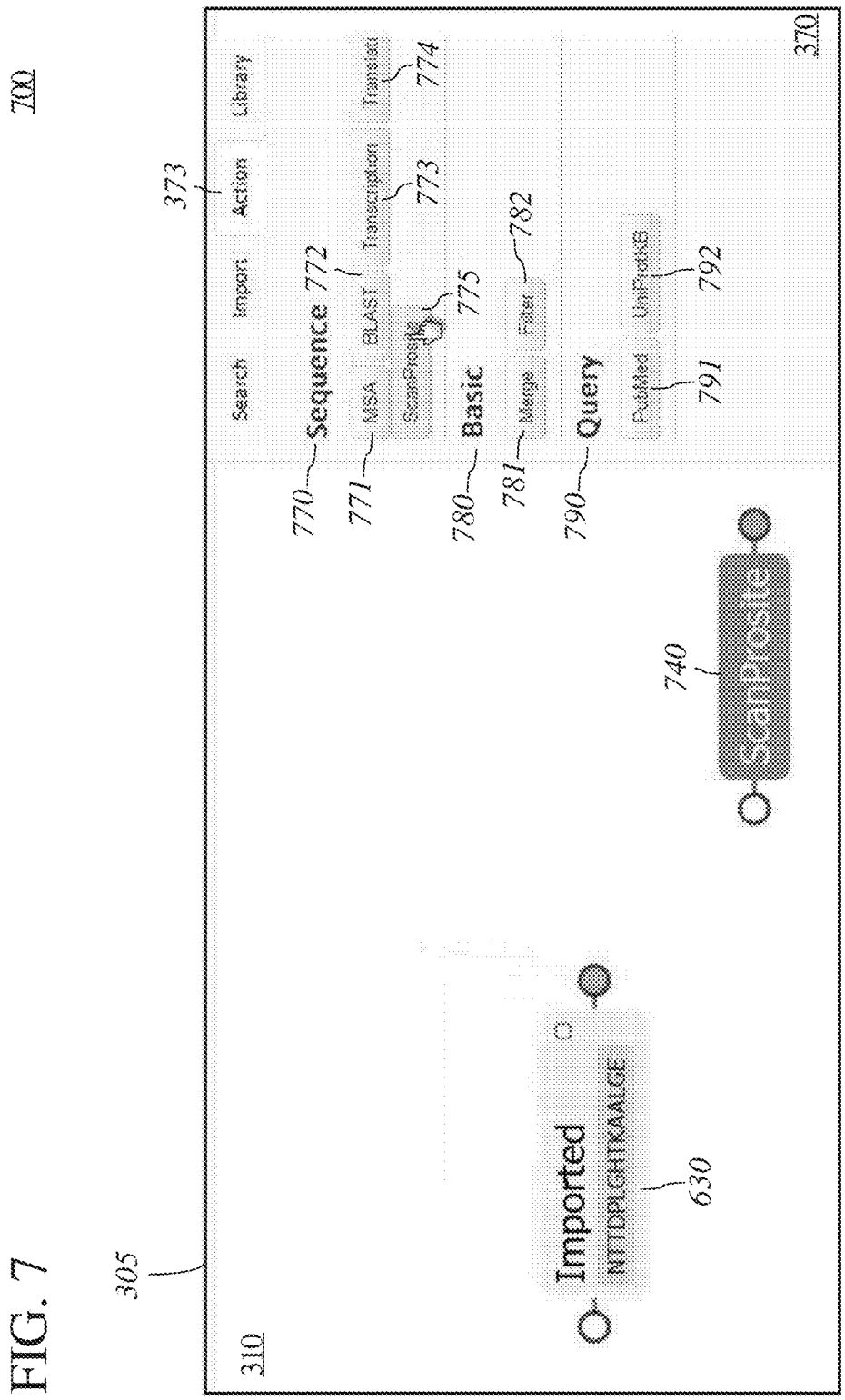
FIG. 7 is a screenshot that illustrates adding an action node to the workspace of the example interface.

FIG. 7 is a screenshot 700 that illustrates adding an action node 740 to workspace 310 of example interface 305, according to an embodiment. Screenshot 700 shows portions of workspace 310 and sidebar 370. The action pane 373 has been selected in sidebar 370, thus causing sidebar 370 to include control groups 770, 780 and 790. Control groups 770, 780, and 790 include, respectively, controls 771-775, 781-782, and 791-792 for adding action nodes to workspace 310. Workspace 310 includes a representation of the newly added action node 740. Action node 740 may have been created, and its corresponding representation added to workspace 310, in response to selection of control 775 from workspace 370. As depicted, action node 740 is shaded differently from data node 630. In an embodiment, all data nodes are shaded or colored differently from action nodes.

Controls 771-775, 781-782, and 791-792 may have been generated, for example, by scanning one or more plugin directories in which the workflow application expects to find modules. Control groups 770, 780, and 790 may have been generated based on module metadata categorizing each of the module plug-ins. Control group 770 corresponds to a "Sequence" category of modules. Selecting one of its controls 771-775 creates an action node that executes an action implemented by, respectively, an "MSA" module, a "BLAST" module, a "Transcription" module, a "Translation" module, or a "ScanProsite" module. Control group 780 corresponds to a "Basic" category of modules, and includes a merge control 781 and filter control 782. Selecting one of controls 781-782 creates an action node that executes an action implemented by, respectively, a "Merge" module or a "Filer" module. Control group 790 corresponds to a "Query" category of modules. Selecting one of its controls 791-792 creates an action node that executes an action implemented by, respectively, a "PubMed" module or a "UniProtKB" module. Since users may easily create their own modules, and since the workflow application automatically creates controls for any modules that a user creates, control groups 770, 780, and 790 are controls 771-775, 781-782, and 791-792 and are but a small sample of the control groups and controls that may appear in sidebar 370.

Figure 8:
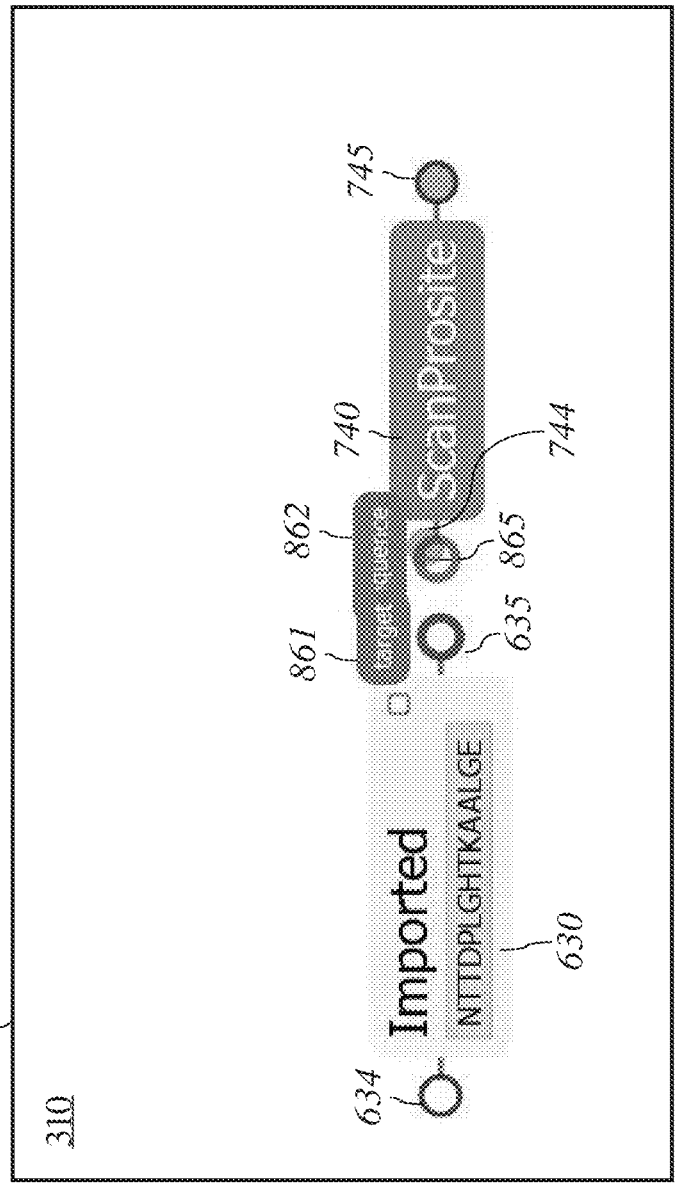
FIG. 8 is a screenshot that illustrates controls for linking nodes in the workspace of the example interface.

FIG. 8 is a screenshot 800 that illustrates controls for linking nodes in the workspace 310 of the example interface 305, according to an embodiment. Screenshot 800 shows a portion of workspace 310, including representations of nodes 630 and 740. The representation of node 740 has been moved closer to the representation of node 630 in response to user input, such as user input that drags and drops node 740 in the currently indicated position. Node 630 includes an input connector 634 and output connector 635. Similarly, node 740 includes an input connector 744 and an output connector 745.

In an embodiment, a user may link any node to any other node by dragging its output connector to the input connector of the other node, or by dragging its input connector to the output connector of the other node. The node whose output connector was connected to the input connector of the other node provides input to the other node, and is thus considered to have been ordered before the other node in the series.

As depicted in FIG. 8, the output connector 635 of node 630 is being dragged to the input connector 744 of node 740. Connector 635 has changed colors, and cursor 865 has been shaped as a connector, to indicate that the user is currently dragging connector 635. Connector labels 861 and 862 also appear while the user is dragging connector 635, providing information about the selected connector and other connectors, as appropriate. In an embodiment, a connector can only be linked to another connector if the two connectors are associated with a same data type. To assist a user in recognizing which connectors are associated with the same data types, user interface 305 may furthermore change the appearance of any connector that is compatible with the connector that is currently selected. Two connectors are compatible if they are of opposite connection types (input versus output), support at least one common data type, are not in the same node, and are not both in data nodes. Hence, since input connector 744 is compatible with output connector 635, input connector 744 has been shaded a solid color with no border, in contrast to input node 634 which is transparent and has a border. Connector 745 likewise has a border, indicating that it cannot receive connector 635. However, node 745 is currently shaded because it represents output that is currently not being provided to another node. A variety of other techniques for changing appearances of compatible nodes may also or instead be utilized.

Figure 9:
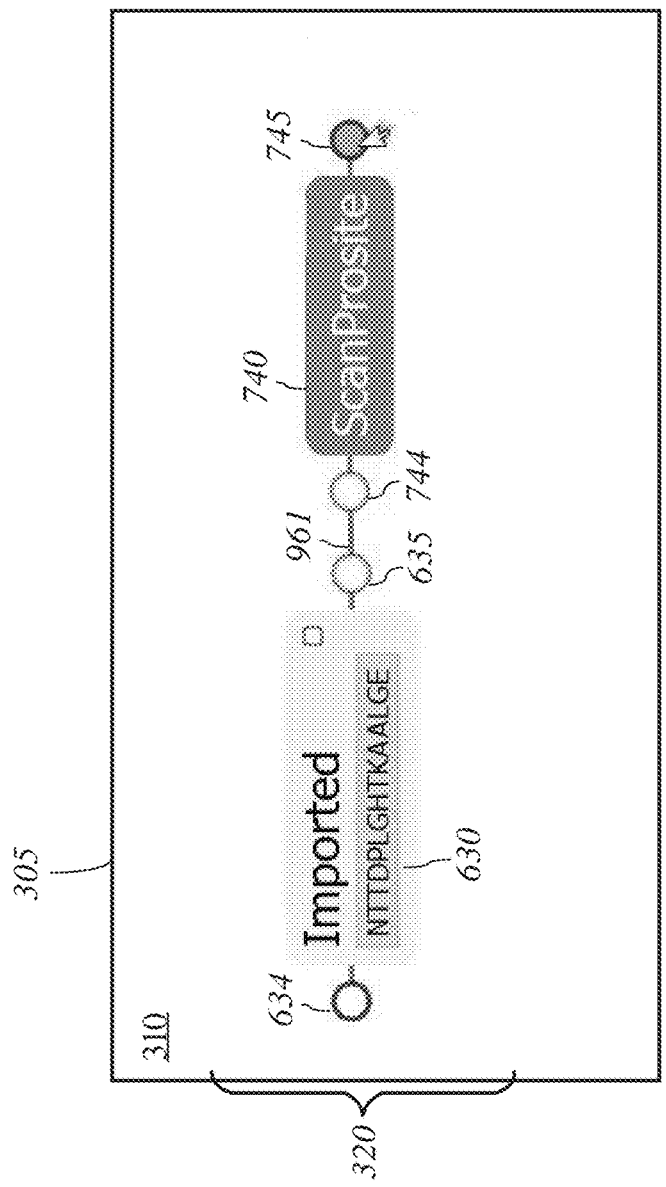
FIG. 9 is a screenshot that illustrates linked nodes in the workspace of the example interface.

FIG. 9 is a screenshot 900 that illustrates linked nodes in the workspace 310 of the example interface 305, according to an embodiment. Screenshot 900 shows a portion of workspace 310, in which nodes 630 and 740 have been linked per the drag and drop operation described above. Workspace 310 includes a representation of the link 961 between nodes 630 and 740. Nodes 630 and 740 now form a series, and as such constitute a functional workflow 320.

Figure 10:
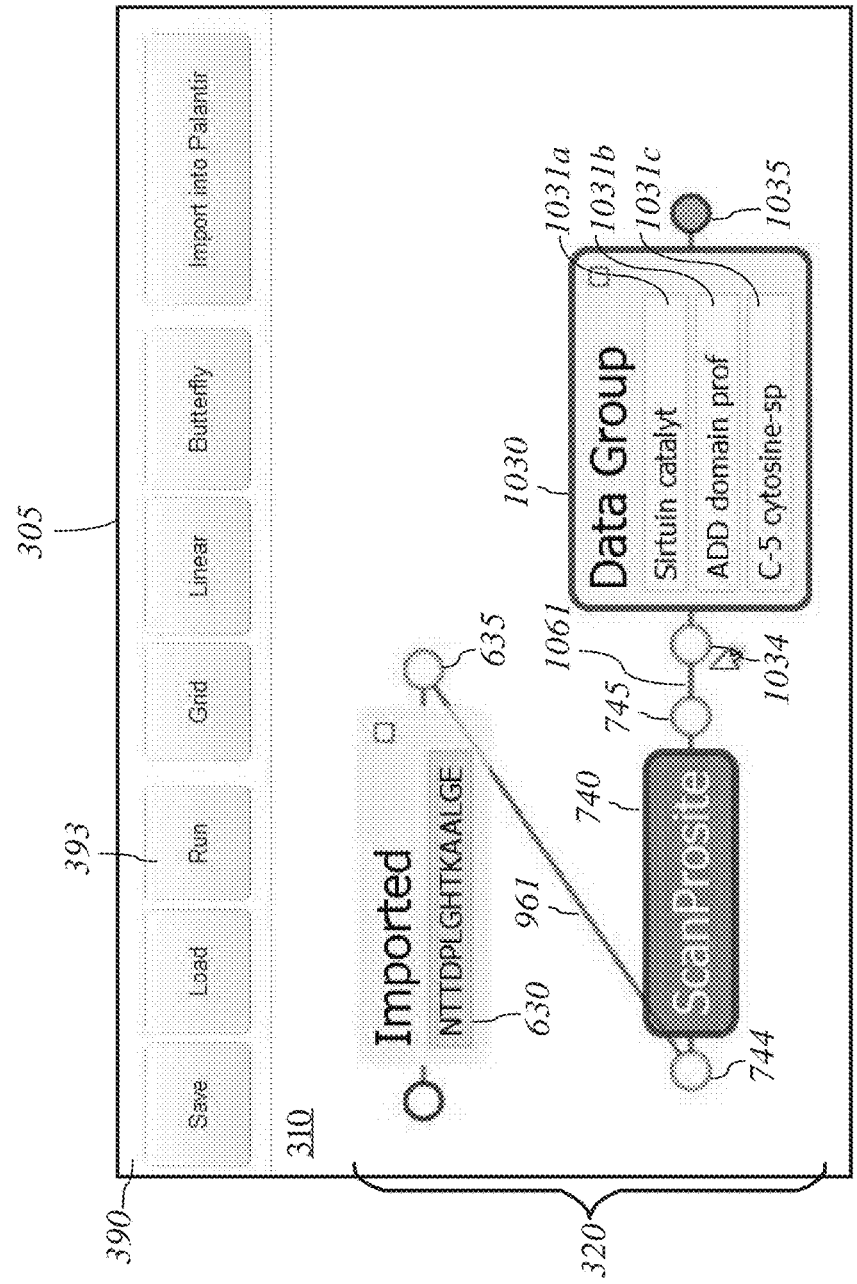
FIG. 10 is a screenshot that illustrates running a portion of the workflow using the example interface.

FIG. 10 is a screenshot 1000 that illustrates running a portion of the workflow 320 using the example interface 305, according to an embodiment. Screenshot 1000 shows header area 390 and a portion of workspace 310, including nodes 630 and 740. After having linked nodes 630 and 740, a user may decide to run workflow 320. Hence, the user may click on the run control 393. In response, the workflow application may run workflow 320 by inputting the sequence represented by node 630 into the ScanProsite module represented by node 740, and executing the ScanProsite module. The ScanProsite module, in turn, interacts with a web server that implements an algorithm for identifying motifs in the sequence. The ScanProsite module receives a response from the web server, interprets this response as a data set of motifs, and provides this data set to the workflow application. The workflow application creates data node 1030, adds the identified motifs to the data node 1030 as data items 1031a-1031c, adds data node 1030 to the workflow 320 by linking data node 1030 to node 740 with a new link 1061, and then adds corresponding representations of the new data to workspace 310. These representations are depicted within workspace 310 of FIG. 10.

Figure 11:
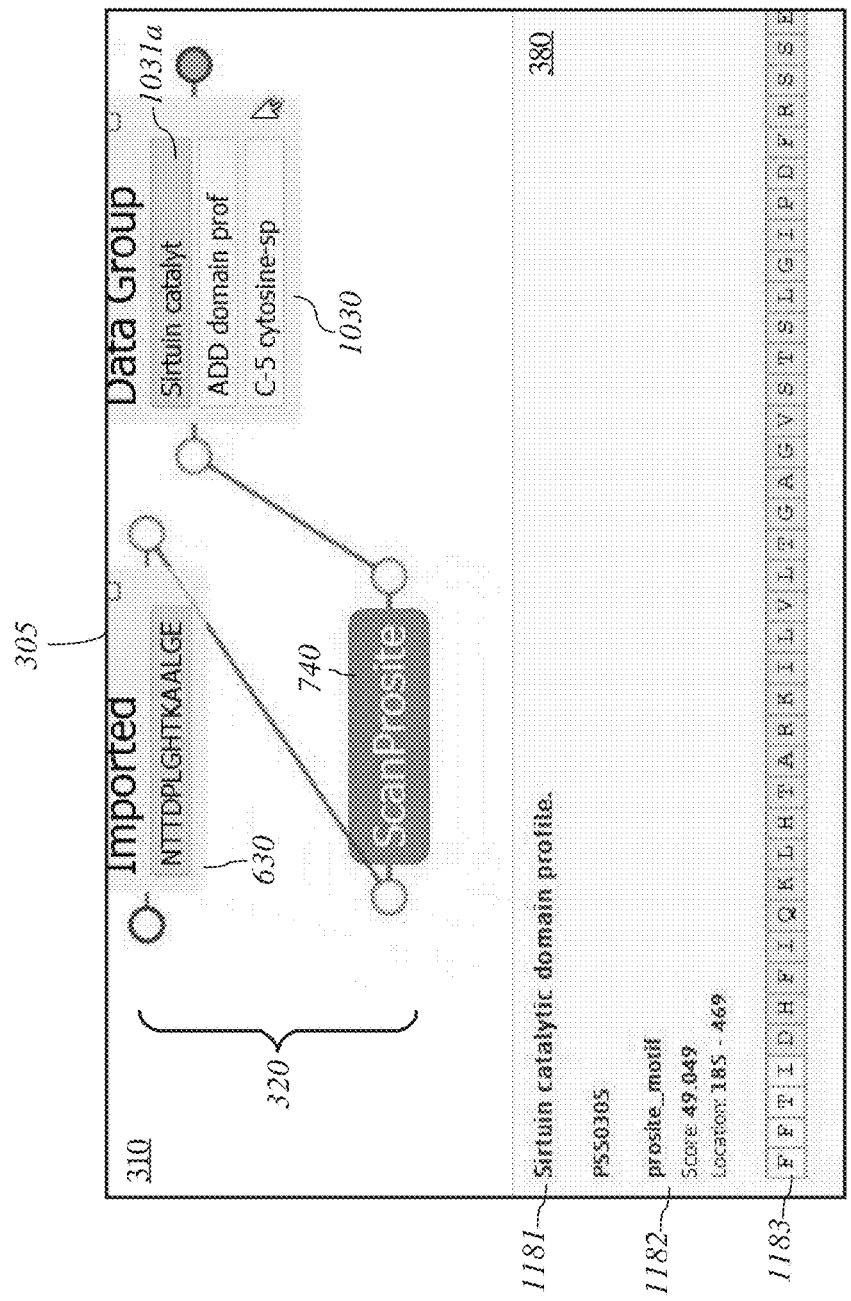
FIG. 11 is a screenshot that illustrates interacting with output from an action node in workflow using the example interface.

FIG. 11 is a screenshot 1100 that illustrates interacting with output from an action node in workflow 320 using the example interface 305, according to an embodiment. Screenshot 1100 shows portions of summary view area 380 and workspace 310, including workflow 320 as constituted in FIG. 10. A particular data item 1031a has been selected from node 1030. In response, summary view area 380 is updated with information associated with item 1031a, including a label 1181, metadata 1182, and a sequence 1183.

Figure 12:
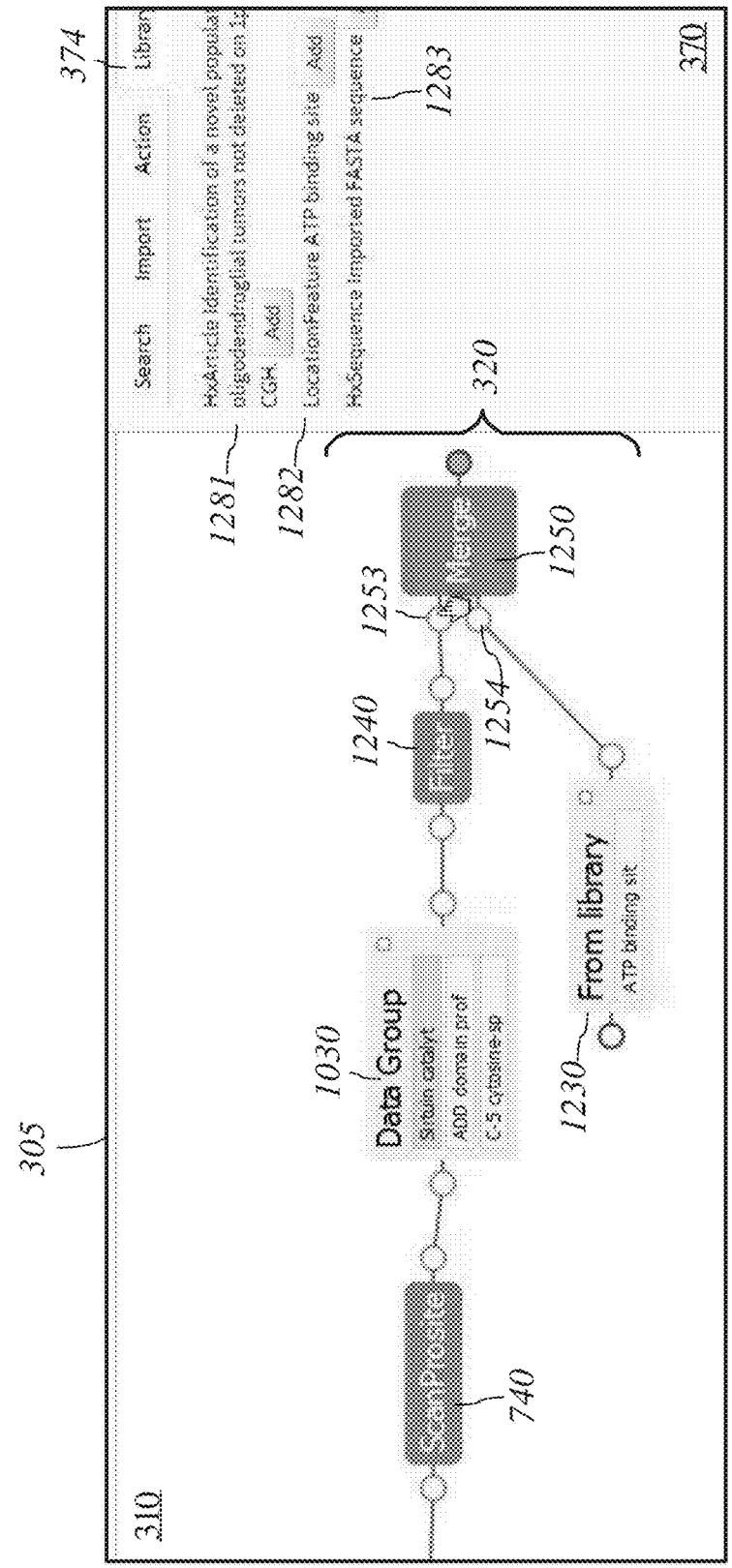
FIG. 12 is a screenshot that illustrates the workspace with various types of nodes from workflow.

FIG. 12 is a screenshot 1200 that illustrates the workspace 310 with various types of nodes from workflow 320, according to an embodiment. Screenshot 1200 shows portions of sidebar 370 and workspace 310. While node 630 has been scrolled out of view in workspace 310, workspace 310 now includes a number of additional nodes that have been added to workflow 320. Specifically, node 1030 is now linked as input to an action node 1240, which is in turn linked as input to action node 1250. Another data node 1230 has also been added to workspace 310. Data node 1230 is also connected as input to action node 1250.

The library pane 374 is selected in sidebar 370. Consequently, sidebar 370 includes three controls 1281-1283 for adding items from a library. In an embodiment, a library is a local storage repository where users may save data items of interest to the user. Hence, sidebar 370 may include many more controls depending on which items have been added by a user. In an embodiment, library items are shared with groups of users. Each control 1281-1283 corresponds to a different library item. Selection of one of controls 1281-1283 results in the addition of the corresponding library item to the currently selected data node, or in the creation of a new data node if no compatible data node is selected. For example, data node 1230 was created when the user clicked on control 1282.

Action node 1240 corresponds to a filter module. For example, action node 1240 may have been added to workspace 310 in response to a user clicking on control 782. By default, the filter module is configured to filter data node 1030 to include only the first item 1031a, but the user may reconfigure the filtering behavior associated with action node 1240 by selecting node 1240 and changing parameter values that are shown in summary view area 380 in response to the selection.

Action node 1250 corresponds to a merge module. For example, action node 1250 may have been added to workspace 310 in response to a user clicking on control 781. Action node 1250 includes multiple input connectors 1253 and 1254, to allow node 1250 to receive multiple inputs. The merge module is configured to create one data set out of the multiple inputs. For example, as depicted, node 1250 will merge the output of node 1240 with the data in node 1230.

Figure 13:
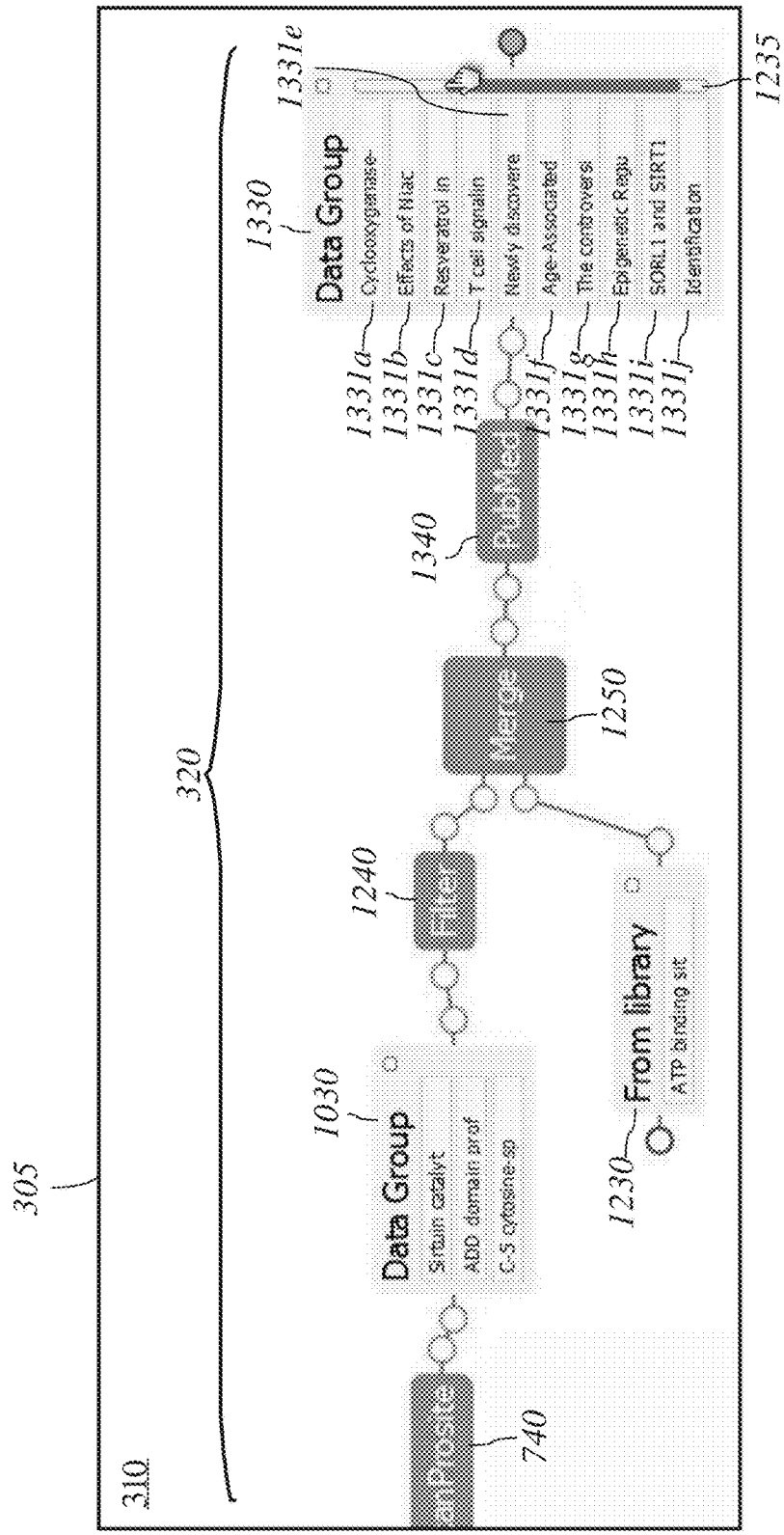
FIG. 13 is a screenshot that illustrates an automated chain of nodes for retrieving publications from a database using the user interface.

FIG. 13 is a screenshot 1300 that illustrates an automated chain of nodes for retrieving publications from a database using user interface 305, according to an embodiment. Screenshot 1300 shows a portion of workspace 310, including most of workflow 320. Workflow 320 now includes an action node 1340 and a data node 1330. Action node 1340 receives the output of merge node 1250 and sends the output to a module for searching a PubMed database for articles. Action node 1340 was generated in response to a user selecting control 791.

After adding action node 1340, the user ran the workflow 320 to generate output for action node 1340. This output, comprising a group of publications, was saved in data node 1330 as at least data items 1331*a*-1331*j*. A user may see other data items that are in node 1330 using scroll control 1235.

Figure 14:
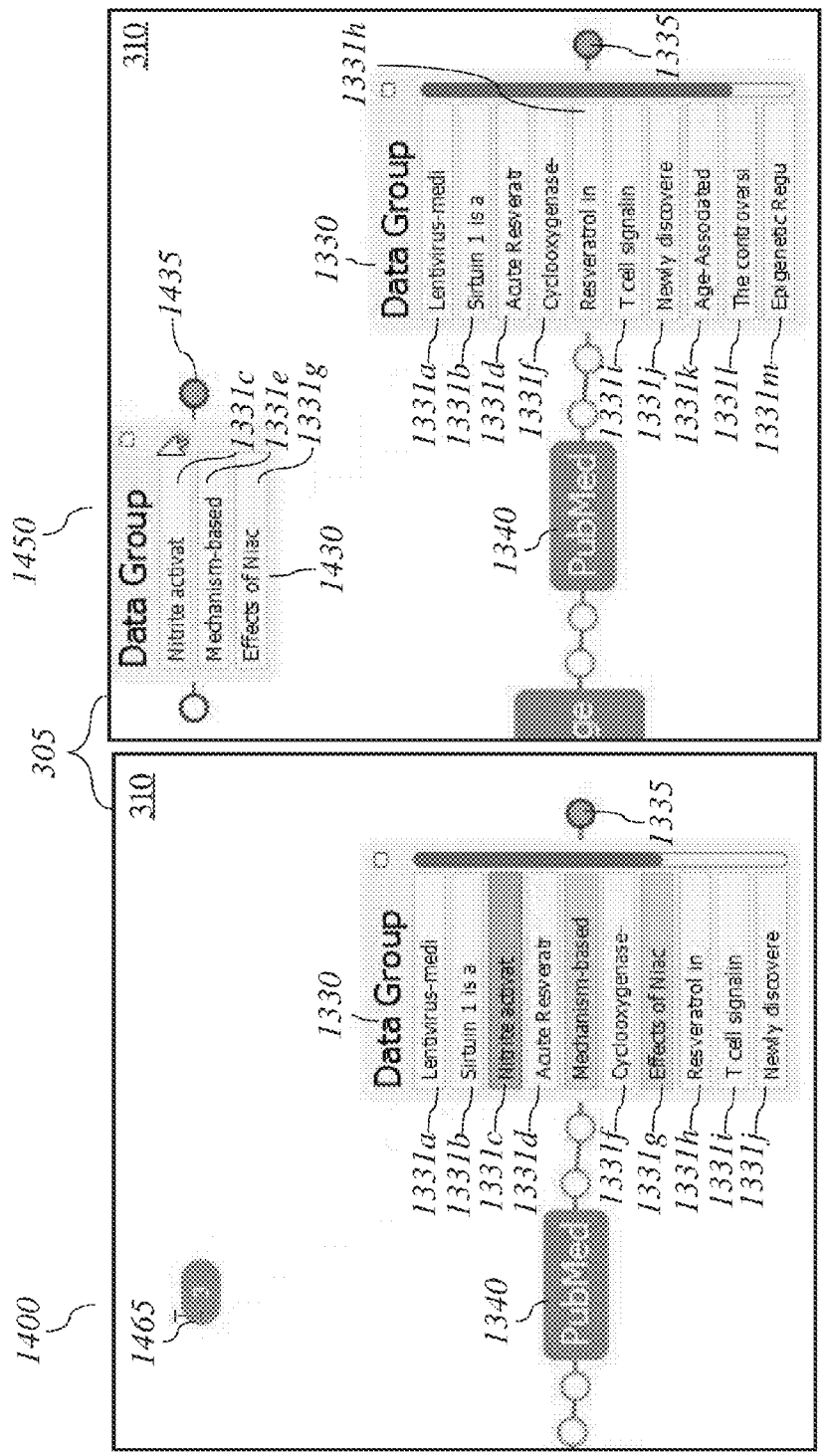
FIG. 14 is a pair of screenshots that illustrate the splitting of data from a data node to create a new data node in the workspace of the user interface.

FIG. 14 is a pair of screenshots 1400 and 1450 that illustrate the splitting of data from data node 1330 to create a new data node 1430 in workspace 310 of user interface 305, according to an embodiment. Screenshots 1400 and 1450 show respectively a portion of workspace 310 while the user is performing the splitting, and the same portion of workspace 310 after the user has performed the splitting. In screenshot 1400, the user has selected three items from data node 1330: items 1331*c*, 1331*e*, and 1331*g*. The user is dragging those items from node 1330 to an empty space in workspace 310. Cursor icon 1465 indicates the current position of the cursor within the workspace, as well as the number of items that the cursor is dragging.

In screenshot 1450, the user has "dropped" the selected items at the location of data node 1430. Accordingly, node 1430 was created and a representation of the node, including data items 1331*c*, 1331*e*, and 1331*g* was added to the workspace 310. Meanwhile, data items 1331*c*, 1331*e*, and 1331*g* are removed from data node 1330 as a result of the operation, rendering items 1331*k-m* visible in node 1330. In some embodiments, however, splitting items from a node does not necessarily remove items from the original node, but rather clones the items in a new node.

Node 1430 can now be added to workflow 320. For example, it may be connected back to node 1340, effectively requesting that node 1340 split its input into two separate data nodes. Or node 1430 may be used as a first node within another independent series of nodes within workflow 320.

Interface 305 is but one example of an interface for practicing techniques described herein. Other interfaces may comprise fewer or additional elements in potentially varying arrangements.

5.0. Example Workflow Action Nodes

Examples of action nodes that may be useful for processing genomic data are described below. There may in fact be many more types of modules than those listed here. Workflows for other types of data may include some of these action nodes, but may also or instead include other action nodes that reflect algorithms for processing the other types of data.

In an embodiment, standard modules include a merge module for merging data sets from multiple nodes and a filter module for filtering a data set based on configurable criteria.

In an embodiment, one type of action node corresponds to a "Translate DNA to Protein" module. The module accepts input in the form of a sequence. The module uses a locally-implemented algorithm to translate the DNA sequence. The module generates output in the form of a protein data structure. Example configurable parameters for the module may include, without limitation, a frame parameter and a complement parameter.

In an embodiment, another type of action node corresponds to a "multiple sequence alignment" module. The module accepts input in the form of a multiple sequence data set in, for example, a multi-FASTA formatted file. The module generates output in the form of alignment data, such as in an MSA alignment file. A summary area of a workflow might present the alignment data in a detailed view area using techniques such as described in the previously referenced application, "Computer Graphical User Interface Supporting Aligning Genomic Sequences."

In an embodiment, another type of action node corresponds to a "Protein family (Pfam) Scan" module. The module accesses a web-based application server that runs a Hidden Markov Module over a protein sequence and computes the most likely protein famil(ies) based on motifs in the protein sequence. The module accepts input in the form of a protein data structure. The module generates output in the form of protein family data structure(s).

In an embodiment, another type of action node corresponds to a "Glimmer" module. The module accesses a web-based application server to locate genes using an interpolated Markov model. Configurable parameters for the module include, without limitation, a genetic code type, topology type, a number of input sequences, and an output data type, which may be an annotation or a sequence.

In an embodiment, another type of action node corresponds to a "BLAST" module. The module accesses a web-based application server that searches for genes in a sequence query using various libraries of genomic data. The module returns information about matching results.

In an embodiment, another type of action node corresponds to a "FASTA sequence reader" module, which converts FASTA file structure into a protein or DNA sequence using a local application.

In an embodiment, another type of action node corresponds to a "UniProt" module. The module queries an online UniProt database to retrieve information about inputted protein sequences or objects. Configurable parameters for the module include, without limitation, an organism parameter, a Gene Ontology (GO) parameter, a reviewed parameter, and a prosite parameter.

In an embodiment, another type of action node corresponds to a "PubMed" module. The module queries the online PubMed database for all publications that match input data. Configurable parameters for the module include, without limitation, an id parameter and a reviewed parameter.

In an embodiment, various workflow node types supported by the systems described herein may include, without limitation, nodes that represent one or more of the following: sourcing functions that retrieve data from one or more sources using various querying and/or scraping techniques; aggregation functions, such as cumulative and average results of data; filtering functions that choose subsets from sets of biological objects based on various matching criteria and/or thresholds; sequence partitioning functions that select a section from a sequence or alignment and use that section as a new data object; comparison functions that compare two or more biological objects or sets of objects based on specified metric(s) and determine whether the differences are statistically significant; comparison functions that compare patient cohorts; conversion and modification functions; sequence alignment generation functions; sequence alignment analysis functions; prediction functions that predict sites of a sequence of potential interest for annotations or other features; annotation functions for automatically creating annotations; annotation lookup functions; Natural Language Processing functions for publications; lookup functions to identify diseases associated with certain genomic objects; and storage functions that save various annotations or other outputs to various storage locations and make the outputs available to other users.

In an embodiment, other example modules to which various workflow node types may link include, without limitation, modules that implement the following types of analyses: allele tests, genotypes frequencies tests, Hardy-Weinberg equilibrium tests, missing genotype rates, inbreeding tests, identity-by-state and identity-by-descent statistics for individuals and pairs of individuals, non-Mendelian transmission in family data, complete linkage hierarchical clustering, multidimensional scaling analysis to visualise substructures, significance tests for whether two individuals belong to the same population, constrain cluster solutions by phenotype, cluster size, and/or external matching criteria, subsequent association analyses that are conditional on cluster solutions, standard allelic tests, Fisher's exact tests, Cochran-Armitage trend tests, Mantel-Haenszel and Breslow-Day tests for stratified samples, dominant/recessive and general model tests, model comparison tests (e.g. general versus multiplicative), family-based association tests such as transmission disequilibrium tests or sibship tests, quantitative traits, associations, and interactions, association tests that are conditional on one or more single-nucleotide polymorphisms ("SNPs"), asymptotic and empirical p-values, flexible clustered permutation schemes, analysis of genotype probability data and fractional allele counts (post-imputation), conditional haplotype tests, case/control and transmission disequilibrium test association on the probabilistic haplotype phase, proxy association methods to study single SNP associations in their local haplotypic context, imputation heuristics to test untyped SNPs given a reference panel, joint SNP and copy-number variation ("CNV") tests for common copy number variants, filtering and summary procedures for segmental (rare) CNV data, case/control comparison tests for global CNV properties, permutation-based association procedure for identifying specific loci, gene-based tests of association, screen for epistasis, gene-environment interaction with continuous and dichotomous environments, and/or fixed and random effects models.

6.0. Example Use Cases

The following examples illustrate how a user may utilize a workflow to simplify various objectives related to genomic data. The examples are given for illustrative purposes only, and not by way of limitation as to the type of objectives to which workflows may be applied. There are, of course, many other types of workflows not described below, including without limitation workflows for epigenetics, effects of copy-number variations, evolutionary biology, and non-coding RNA analysis.

6.1. Gene Annotation

One use for the workflows described herein is to address gene annotation problems. For example, *Lactobacillus acidophilus* strains, which are typically of interest in probiotics and potential vaccine vectors, sometimes have a surface layer protein for adhesion to cells. A researcher may sequence a new strain of *L. acidophilus*. When the researcher aligns the new strain to the reference sequences, the researcher discovers that the new strain lacks the SlpA gene, but has an unknown insertion. The researcher decides that the new strain may be interesting, and wants to know whether the new strain is a gene, the likely function of the protein that the new strain encodes, the biological context of the new strain, and how the strain compares to proteins that are already known.

An example workflow to assist in accomplishing these objectives may be as follows. A first set of one or more action nodes loads the appropriate DNA sequence and metadata, including the source, sequencing method, date, and quality. A second set of one or more action nodes runs a GLIMMER tool to predict gene(s) based on the loaded data. A third set of one or more action nodes runs a multi-sequence alignment and comparison to compare the sequence to a corresponding region of the *L. acidophilus* reference sequence, thereby producing a genome object with annotated genes. A fourth set of one or more action nodes translates the genome object into a protein sequence. A fifth set of one or more action nodes predicts pfams and GO terms. A sixth set of one or more action nodes runs BLAST on the protein sequence to answer the questions of what pfams and GO terms are most common among the top hits, how do these terms intersect with those from the predicted protein, and how closely related are the bacteria of the top hits to *L. acidophilus*? A seventh set of one or more action nodes searches for known pathways that the top hits are involved in using Metacyc and E.C. numbers. An eighth set of one or more action nodes pulls PubMed data for the top BLAST hits. A ninth set of one or more action nodes find genes and features upstream and downstream of the insertion and determines what the functions of these sites are. A tenth set of one or more action nodes runs a feature/annotation module to compare the gene to the PubMed annotations of the BLAST hits to identify unique features of the gene. An eleventh set of one or more action nodes adds appropriate annotations concerning the unique feature as annotations to the gene, and links the annotations back to the genome.

In an embodiment, various actions may require human intervention to identify important data points before proceeding to the next node. In an embodiment, the workflow is entirely automated, without human intervention. In an embodiment, such a workflow may be saved for reuse. The next time the researcher discovers a new strain, the researcher may perform the same workflow with respect to the new strain simply by modifying the original workflow input.

6.2. Sequence-Structure-Function-Disease

Another use for the workflows described herein is to address sequence-structure-function-disease problems with respect to a gene. For example, a researcher may put together a workflow that answers questions such as what are the implications of the polymorphisms in a gene for how and when the gene is expressed, what are the implications of the polymorphisms in the protein it encodes for interaction with its co-factor, and how do these implications relate to the gene's role in disease.

An example workflow to assist in accomplishing these objectives may be as follows. A first set of one or more action nodes performs a multi-sequence alignment of the gene's variants. A second set of one or more action nodes uses tracked viewing of microarray expression data under various experimental conditions to identify patterns of altered activity. The identification process may involve multiple-hypothesis controlled t-tests and/or other algorithms to statistically identify mutations that are correlated with expression changes under one or more conditions. A third set of one or more action nodes adds a track of annotated features, such as regulatory sequences, to compare with the experimental expression data. A fourth set of one or more action nodes performs a multi-sequence alignment of the protein's variants. A fifth set of one or more action nodes performs a tracked viewing of activity levels, such as binding affinity. A sixth set of one or more action nodes examines individual assays in a table view module to determine the ranking of the variants by binding affinity. A seventh set of one or more action nodes uses a structure viewer module to assess how binding affinity might be affected by amino acid mutations, including predicting important interactions (H-bonds, pi-pi interactions, steric interactions). An eighth set of one or more action nodes searches PubChem for additional relevant assays. A ninth set of one or more action nodes looks up the pathways that the protein is in. A tenth set of one or more action nodes searches PubMed for items associated with both the gene and a disease. An eleventh set of one or more action nodes imports the other components of the biological pathway hypothesized to link gene and disease from Uniprot and/or other databases and draws the biological pathway.

6.3. Protein Design

Another use for the workflows described herein is to address protein design problems. For example, a researcher may intend to design a set of candidate proteins to perform a specific chemical function, such as tyrosine decarboxylase. The researcher will have these proteins made, and then try them out in a bacterium that lacks this activity.

An example workflow to assist in accomplishing these objectives may be as follows. A first set of one or more action nodes searches Uniprot for proteins with pfam PF00282 (Pyridoxal-dependent decarboxylase). A second set of one or more action nodes searches Pfam for PF00282 and unions the results with the Uniprot results. A third set of one or more action nodes runs BLAST on this set of protein sequences against itself to generate all possible pairwise BLAST comparisons. A fourth set of one or more action nodes clusters the results based on the BLAST scores. A fifth set of one or more action nodes looks at the annotations from each cluster and determines if there is more than one cluster annotated with tyrosine decarboxylase activity. A sixth set of one or more action nodes aligns the sequences from each cluster, annotated with Y-decarb activity. The alignment accomplishes two objectives. First, the alignment allows for a comparison of the conserved regions within and between alignments. Second, the alignment groups subsets of aligned sequences, visually or algorithmically, based on similarity. A seventh set of one or more action nodes creates a set of candidate proteins that is representative of the alignments, in that the candidate proteins have a consensus sequence in the conserved regions. An eighth set of one or more action nodes looks at the bacteria that produce the BLAST hit proteins and determines which bacteria is most similar to the researcher's test bacterium, based on phylogenetic information. This may entail calling the Y-decarb from a bacterium candidate1, adding candidate1 to the list of candidate proteins, and filling in the non-conserved regions of the other candidates with the sequence from candidate1. A ninth set of one or more action nodes searches PubMed or other databases for comparisons of the niche and metabolism of the two species. A tenth set of one or more action nodes searches PubMed or other databases to find what more is known about candidate1 in the other bacterium. An eleventh set of one or more action nodes analyzes the annotated features from candidate1 to hypothesize whether any regions will be disrupted in the other candidates. A twelfth set of one or more action nodes analyzes the structure of candidate1 and alignment of each other candidate to candidate1, to determine where the sequence changes might impact structure. This may involve threading the candidate sequences into the structure of candidate1, or threading both into the most similar existing PDB structure, and finding differences. A thirteenth set of one or more action nodes exports the sequences of the candidate proteins to a database for future reference.

6.4. Genome-Wide Association Study

Another use for the workflows described herein is for Genome-Wide Association Studies. For example, a researcher may be curious as to which SNPs (if any) in a set of genomes are associated with the incidence of a disease. The researcher has a set of individuals in varying disease states, as measured by a biomarker concentration. All of the individuals are genotyped using a SNP chip with 1 million SNPs. Quality control has already been performed.

An example workflow to assist in accomplishing the Genome-Wide Association Studies is as follows. A first set of one or more action nodes uses Plink, Eigenstrat, and/or R modules to compute summary statistics, including allele frequencies and SNP frequencies. A second set of one or more action nodes uses these same modules to adjust the statistics to control for population stratification (i.e. bias due to ancestry/relatedness within the case or control group), using identity-by-state (IBS) or multidimensional scaling. A third set of one or more action nodes uses these modules to run a variety of association tests, in order to determine how the genotype is linked to disease. The tests include Fisher's exact test, Chi square, correlation, and regression. More specifically, the following analyses may be performed: Basic Allelic (how is each allele associated), Genotypic Tests (how is each pair of alleles associated), Additive Model (does having two of an allele, versus none, have twice the effect as having one, versus none), Dominant Model (at least one of the minor allele versus none), Recessive Model (two minor alleles versus one or none). A fourth set of one or more action nodes uses a Manhattan plot module, potentially with a ggplot2 R package, to generate a plot of the p-values of all the SNPs along the genomic axis. A fifth set of one or more action nodes extracts SNPs with a p-value, after multiple hypothesis correction, below a threshold (e.g. $p=10^{\wedge}-8$). A sixth set of one or more action nodes generates multiple sequence alignments of each SNP's region. The multiple sequence alignments are organized by case/control. A seventh set of one or more action nodes searches dbSNP or other databases for the SNPs to determine if they have they been associated with anything else. An eighth set of one or more action nodes searches for other annotations in these regions, in order to form functional hypotheses.

7.0. Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 15:
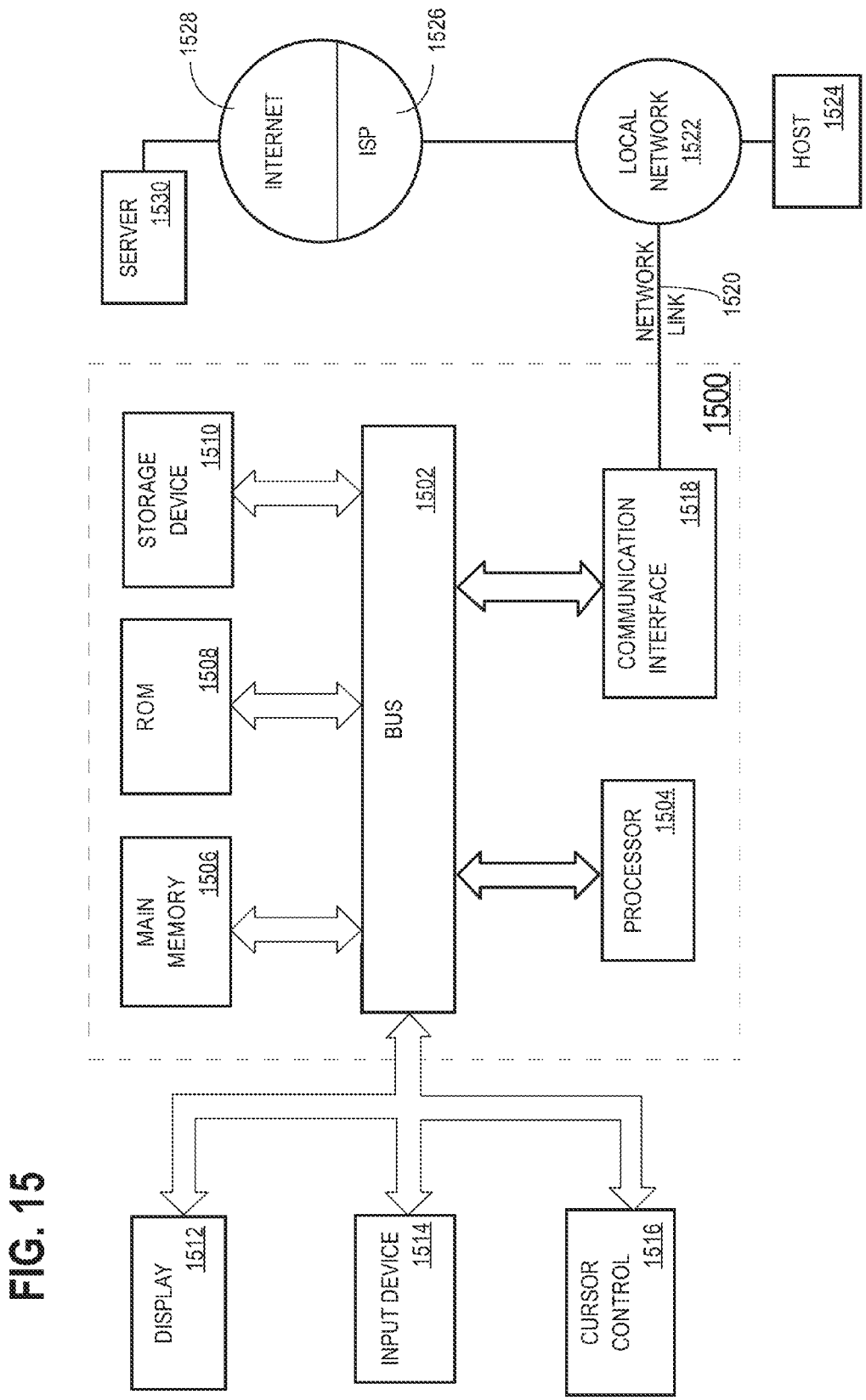
FIG. 15 is a block diagram that illustrates a computer system upon which an embodiment of the invention may be implemented.

For example, FIG. 15 is a block diagram that illustrates a computer system 1500 upon which an embodiment of the invention may be implemented. Computer system 1500 includes a bus 1502 or other communication mechanism for communicating information, and a hardware processor 1504 coupled with bus 1502 for processing information. Hardware processor 1504 may be, for example, a general purpose microprocessor.

Computer system 1500 also includes a main memory 1506, such as a random access memory (RAM) or other dynamic storage device, coupled to bus 1502 for storing information and instructions to be executed by processor 1504. Main memory 1506 also may be used for storing temporary variables or other intermediate information during execution of instructions to be executed by processor 1504. Such instructions, when stored in non-transitory storage media accessible to processor 1504, render computer system 1500 into a special-purpose machine that is customized to perform the operations specified in the instructions.

Computer system 1500 further includes a read only memory (ROM) 1508 or other static storage device coupled to bus 1502 for storing static information and instructions for processor 1504. A storage device 1510, such as a magnetic disk or optical disk, is provided and coupled to bus 1502 for storing information and instructions.

Computer system 1500 may be coupled via bus 1502 to a display 1512, such as a cathode ray tube (CRT), for displaying information to a computer user. An input device 1514, including alphanumeric and other keys, is coupled to bus 1502 for communicating information and command selections to processor 1504. Another type of user input device is cursor control 1516, such as a mouse, a trackball, or cursor direction keys for communicating direction information and command selections to processor 1504 and for controlling cursor movement on display 1512. This input device typically has two degrees of freedom in two axes, a first axis (e.g., x) and a second axis (e.g., y), that allows the device to specify positions in a plane.

Computer system 1500 may implement the techniques described herein using customized hard-wired logic, one or more ASICs or FPGAs, firmware and/or program logic which in combination with the computer system causes or programs computer system 1500 to be a special-purpose machine. According to one embodiment, the techniques herein are performed by computer system 1500 in response to processor 1504 executing one or more sequences of one or more instructions contained in main memory 1506. Such instructions may be read into main memory 1506 from another storage medium, such as storage device 1510. Execution of the sequences of instructions contained in main memory 1506 causes processor 1504 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 1510. Volatile media includes dynamic memory, such as main memory 1506. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 1502. Transmission media can also take the form of acoustic or light waves, such as those generated during radio-wave and infra-red data communications.

Various forms of media may be involved in carrying one or more sequences of one or more instructions to processor 1504 for execution. For example, the instructions may initially be carried on a magnetic disk or solid state drive of a remote computer. The remote computer can load the instructions into its dynamic memory and send the instructions over a telephone line using a modem. A modem local to computer system 1500 can receive the data on the telephone line and use an infra-red transmitter to convert the data to an infra-red signal. An infra-red detector can receive the data carried in the infra-red signal and appropriate circuitry can place the data on bus 1502. Bus 1502 carries the data to main memory 1506, from which processor 1504 retrieves and executes the instructions. The instructions received by main memory 1506 may optionally be stored on storage device 1510 either before or after execution by processor 1504.

Computer system 1500 also includes a communication interface 1518 coupled to bus 1502. Communication interface 1518 provides a two-way data communication coupling to a network link 1520 that is connected to a local network 1522. For example, communication interface 1518 may be an integrated services digital network (ISDN) card, cable modem, satellite modem, or a modem to provide a data communication connection to a corresponding type of telephone line. As another example, communication interface 1518 may be a local area network (LAN) card to provide a data communication connection to a compatible LAN. Wireless links may also be implemented. In any such implementation, communication interface 1518 sends and receives electrical, electromagnetic or optical signals that carry digital data streams representing various types of information.

Network link 1520 typically provides data communication through one or more networks to other data devices. For example, network link 1520 may provide a connection through local network 1522 to a host computer 1524 or to data equipment operated by an Internet Service Provider (ISP) 1526. ISP 1526 in turn provides data communication services through the world wide packet data communication network now commonly referred to as the "Internet" 1528. Local network 1522 and Internet 1528 both use electrical, electromagnetic or optical signals that carry digital data streams. The signals through the various networks and the signals on network link 1520 and through communication interface 1518, which carry the digital data to and from computer system 1500, are example forms of transmission media.

Computer system 1500 can send messages and receive data, including program code, through the network(s), network link 1520 and communication interface 1518. In the Internet example, a server 1530 might transmit a requested code for an application program through Internet 1528, ISP 1526, local network 1522 and communication interface 1518.

The received code may be executed by processor 1504 as it is received, and/or stored in storage device 1510, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A method comprising:
    presenting, in a graphical user interface, graphical components representing a source from which one or more nucleic acid sequences are to be obtained and one or more sets of instructions for processing data, including at least one set of instructions for processing the one or more nucleic acid sequences, wherein the source and the one or more sets of instructions are represented as nodes within a workspace;
    wherein the source and the one or more sets of instructions are arranged as a workflow comprising a series of nodes, the series of nodes indicating, for each particular set of instructions of the one or more sets of instructions, that output from one of the source or another particular set of instructions is to be input into the particular set of instructions;
    generating an output for the workflow, wherein the output comprises a set of one or more items of genomic data that are based upon the one or more nucleic acid sequences that are processed by each set of instructions of the one or more sets of instructions in an order indicated by the series of nodes;
    generating a first data node from the output, the first data node comprising the set of one or more items of genomic data, the first data node linked to a last set of instructions in the series;
    receiving, via the graphical user interface, a first input that selects a subset of one or more items of genomic data from the set of one or more items of genomic data in the first data node;
    receiving, via the graphical user interface, a second input that moves the subset of one or more items of genomic data to a location on the graphical user interface not associated with the first data node;
    generating a second data node comprising the subset of one or more items of genomic data, wherein the output for the workflow is reconfigured to generate multiple data nodes; and
    wherein the method is performed by one or more computing devices.

2. The method of claim 1, wherein each set of instructions of the one or more sets of instructions generates output that conforms to an ontology defining data structures that represent genomic data, the data structures representing at least all of: sequences, protein objects, alignment objects, annotations, and publications.

3. The method of claim 1, further comprising:
    receiving, via the graphical user interface, third input selecting a particular set of instructions to process the first data node;
    adding the particular set of instructions to the end of the series; and
    generating third output for the workflow based upon the one or more nucleic acid sequences by processing each set of instructions in the series, including the particular set of instructions, in the order indicated by the series.

4. The method of claim 1, wherein the one or more sets of instructions comprises at least two sets of instructions, wherein generating the output for the workflow comprises using output from the source as input to a first set of instructions, and using output from the first set of instructions as input to a second set of instructions.

5. The method of claim 1, wherein the at least one set of instructions is configured to process the one or more nucleic acid sequences by communicating with at least one of an external web server or an external database server.

6. The method of claim 1, further comprising:
    saving workflow data describing the series;
    causing the workflow data to be shared with multiple users;
    subsequently reconstructing the series in a second graphical user interface based on the workflow data;
    receiving sixth input, via the second graphical user interface, modifying the series to include one or more additional sets of instructions; and
    generating second output based upon the one or more nucleic acid sequences by processing each set of instructions in the series, including the one or more additional sets of instructions, in an order indicated by the series.

7. The method of claim 1, wherein the one or more sets of instructions include a first set of instructions that generates first output based upon the source, and a second set of instructions that merges the first output with second output from a third set of instructions that is not in the series, wherein the source, first set of instructions, second set of instructions, and third set of instructions are all nodes within a workflow.

8. The method of claim 1, further comprising presenting controls for selecting the one or more sets of instructions, wherein the controls include at least: a first control for selecting a first set of instructions that searches for publications in an online database based on genomic data, a second control for selecting a second set of instructions that outputs a sequence alignment for multiple sequences, and a third control for selecting a third set of instructions that identifies protein families for a nucleic acid sequence.

9. The method of claim 1, wherein receiving the one or more third inputs comprises presenting visual feedback while a first node is selected that indicates that genomic data output from the first node can be linked as input to a second node.

10. The method of claim 1, wherein the one or more sets of instructions comprises at least two sets of instructions, wherein processing each set of instructions of the one or more sets of instructions in an order indicated by the series comprises automatically processing each set of instructions, without human intervention between beginning processing of a first set of instructions in the series and generating the output by concluding processing of a last set of instructions in the series.

11. One or more non-transitory computer-readable media storing instructions that, when executed by one or more computing devices, cause:
    presenting, in a graphical user interface, graphical components representing a source from which one or more nucleic acid sequences are to be obtained and one or more sets of instructions for processing data, including at least one set of instructions for processing the one or more nucleic acid sequences, wherein the source and the one or more sets of instructions are represented as nodes within a workspace;

wherein the source and the one or more sets of instructions are arranged as a workflow comprising a series of nodes, the series of nodes indicating, for each particular set of instructions of the one or more sets of instructions, that output from one of the source or another particular set of instructions is to be input into the particular set of instructions;

generating an output for the workflow, wherein the output comprises a set of one or more items of genomic data that are based upon the one or more nucleic acid sequences that are processed by each set of instructions of the one or more sets of instructions in an order indicated by the series of nodes;

generating a first data node from the output, the first data node comprising the set of one or more items of genomic data, the first data node linked to a last set of instructions in the series;

receiving, via the graphical user interface, a first input that selects a subset of one or more items of genomic data from the set of one or more items of genomic data in the first data node;

receiving, via the graphical user interface, a second input that moves the subset of one or more items of genomic data to a location on the graphical user interface not associated with the first data node;

generating a second data node comprising the subset of one or more items of genomic data, wherein the output for the workflow is reconfigured to generate multiple data nodes.

12. The one or more non-transitory computer-readable media of claim 11, wherein each set of instructions of the one or more sets of instructions generates output that conforms to an ontology defining data structures that represent genomic data, the data structures representing at least all of: sequences, protein objects, alignment objects, annotations, and publications.

13. The one or more non-transitory computer-readable media of claim 11, wherein the instructions, when executed by the one or more computing devices, further cause:
receiving, via the graphical user interface, third input selecting a particular set of instructions to process the first data node;
adding the particular set of instructions to the end of the series; and
generating third output for the workflow based upon the one or more nucleic acid sequences by processing each set of instructions in the series, including the particular set of instructions, in the order indicated by the series.

14. The one or more non-transitory computer-readable media of claim 11, wherein the one or more sets of instructions comprises at least two sets of instructions, wherein generating the output for the workflow comprises using output from the source as input to a first set of instructions, and using output from the first set of instructions as input to a second set of instructions.

15. The one or more non-transitory computer-readable media of claim 11, wherein the at least one set of instructions is configured to process the one or more nucleic acid sequences by communicating with at least one of an external web server or an external database server.

16. The one or more non-transitory computer-readable media of claim 11, wherein the instructions, when executed by the one or more computing devices, further cause:
saving workflow data describing the series;
causing the workflow data to be shared with multiple users;
subsequently reconstructing the series in a second graphical user interface based on the workflow data;
receiving sixth input, via the second graphical user interface, modifying the series to include one or more additional sets of instructions; and
generating second output based upon the one or more nucleic acid sequences by processing each set of instructions in the series, including the one or more additional sets of instructions, in an order indicated by the series.

17. The one or more non-transitory computer-readable media of claim 11, wherein the one or more sets of instructions include a first set of instructions that generates first output based upon the source, and a second set of instructions that merges the first output with second output from a third set of instructions that is not in the series, wherein the source, first set of instructions, second set of instructions, and third set of instructions are all nodes within a workflow.

18. The one or more non-transitory computer-readable media of claim 11, wherein the instructions, when executed by the one or more computing devices, further cause presenting controls for selecting the one or more sets of instructions, wherein the controls include at least: a first control for selecting a first set of instructions that searches for publications in an online database based on genomic data, a second control for selecting a second set of instructions that outputs a sequence alignment for multiple sequences, and a third control for selecting a third set of instructions that identifies protein families for a nucleic acid sequence.

19. The one or more non-transitory computer-readable media of claim 11, wherein receiving the one or more third inputs further cause presenting visual feedback while a first node is selected that indicates that genomic data output from the first node can be linked as input to a second node.

20. The one or more non-transitory computer-readable media of claim 11, wherein the one or more sets of instructions comprises at least two sets of instructions, wherein processing each set of instructions of the one or more sets of instructions in an order indicated by the series comprises automatically processing each set of instructions, without human intervention between beginning processing of a first set of instructions in the series and generating the output by concluding processing of a last set of instructions in the series.

* * * * *